US011250948B2

(12) United States Patent
Li et al.

(10) Patent No.: US 11,250,948 B2
(45) Date of Patent: Feb. 15, 2022

(54) SEARCHING AND DETECTING INTERPRETABLE CHANGES WITHIN A HIERARCHICAL HEALTHCARE DATA STRUCTURE IN A SYSTEMATIC AUTOMATED MANNER

(71) Applicant: International Business Machines Corporation, Armonk, NY (US)

(72) Inventors: Ta-Hsin Li, Danbury, CT (US); Gigi Y. C. Yuen-Reed, Tampa, FL (US); Huijing Jiang, Chappaqua, NY (US); Kevin N. Tran, Marina del Rey, CA (US); Bob Kelley, Ann Arbor, MI (US); Thomas Halvorson, Saline, MI (US)

(73) Assignee: International Business Machines Corporation, Armonk, NY (US)

( * ) Notice: Subject to any disclaimer, the term of this patent is extended or adjusted under 35 U.S.C. 154(b) by 108 days.

(21) Appl. No.: 16/263,601

(22) Filed: Jan. 31, 2019

(65) Prior Publication Data
US 2020/0251205 A1    Aug. 6, 2020

(51) Int. Cl.
G16H 40/20   (2018.01)
G06N 20/00   (2019.01)
G06Q 10/06   (2012.01)

(52) U.S. Cl.
CPC ............. *G16H 40/20* (2018.01); *G06N 20/00* (2019.01); *G06Q 10/06393* (2013.01)

(58) Field of Classification Search
CPC ..... G16H 40/20; G06Q 10/0693; G06N 20/00
(Continued)

(56) References Cited

U.S. PATENT DOCUMENTS 5,937,364 A    8/1999  Westgard et al.
7,050,933 B2   5/2006  Parvin et al.
(Continued)

FOREIGN PATENT DOCUMENTS

CN    109241123 A  *  1/2019

OTHER PUBLICATIONS

Yadav, Pranjul, et al. "Mining electronic health records (EHRs) A survey." ACM Computing Surveys (CSUR) 50.6 (2018): 1-40. (Year: 2018).*

(Continued)

*Primary Examiner* — Jerry O'Connor
*Assistant Examiner* — Jeremy L Gunn
(74) *Attorney, Agent, or Firm* — Will Stock; Edell, Shapiro & Finnan, LLC

(57) ABSTRACT

Computer-implemented methods, systems, and computer readable media are provided for identifying and optimizing performance drivers of a healthcare related system. Healthcare related data may be analyzed to produce performance information pertaining to performance indicators for performance drivers of the healthcare related system. From the performance information, changes in the sets of performance indicators over time for the performance drivers may be determined and performance drivers with determined changes satisfying a threshold may be identified. An impact of the determined changes in the performance indicators to the identified performance drivers and contributions to the determined impact from one or more factors may be identified. Factors of the identified performance drivers with opposing utilization trends may be identified and an impact of the identified factors on the performance drivers may be determined. The identified performance drivers may be ranked and use of the performance drivers may be adjusted based on the ranking.

16 Claims, 26 Drawing Sheets

(58) Field of Classification Search
USPC .................................................... 705/7.39
See application file for complete search history.

(56) References Cited

U.S. PATENT DOCUMENTS

| | | | | |
|---|---|---|---|---|
| 8,364,519 | B1* | 1/2013 | Basu | G06Q 10/0637 |
| | | | | 705/7.38 |
| 2008/0027841 | A1* | 1/2008 | Eder | G06Q 40/00 |
| | | | | 705/35 |
| 2013/0132108 | A1* | 5/2013 | Solilov | G16H 50/70 |
| | | | | 705/2 |
| 2013/0173355 | A1* | 7/2013 | Barcenas | G06Q 10/06393 |
| | | | | 705/7.39 |
| 2013/0332194 | A1* | 12/2013 | D'Auria | G16H 10/60 |
| | | | | 705/3 |
| 2014/0282600 | A1* | 9/2014 | Siepmann | G06F 9/5066 |
| | | | | 718/106 |
| 2015/0149235 | A1 | 5/2015 | Leung | |
| 2015/0317337 | A1 | 11/2015 | Edgar | |
| 2016/0019357 | A1 | 1/2016 | Marzula et al. | |
| 2016/0292611 | A1* | 10/2016 | Boe | H04L 41/5009 |
| 2017/0140393 | A1 | 5/2017 | Katz-Rogozhnikov et al. | |
| 2017/0169173 | A1 | 6/2017 | Snow et al. | |
| 2017/0278171 | A1 | 9/2017 | Tapia | |
| 2018/0024901 | A1 | 1/2018 | Tankersley et al. | |
| 2018/0121390 | A1* | 5/2018 | Tzabari | G06K 9/00536 |
| 2018/0246944 | A1* | 8/2018 | Yelisetti | G06F 16/258 |
| 2018/0262618 | A1* | 9/2018 | Stern | G06Q 10/06398 |
| 2018/0330302 | A1* | 11/2018 | Peterson | G10L 25/66 |
| 2020/0019822 | A1* | 1/2020 | Kothandaraman | G06K 9/6253 |
| 2020/0118653 | A1* | 4/2020 | Hagenbuch | G16H 10/60 |
| 2020/0250160 | A1* | 8/2020 | Jedrzejewski | G16H 40/67 |

OTHER PUBLICATIONS

English translation of application CN 109241123 A, retrieved from espacenet.com on Sep. 9, 2021 (Year: 2019).*
Roski, J. et al., "Creating value in health care through big data: opportunities and policy implications", Health affairs, 33(7), 2014, pp. 1115-1122.
Gandy, A. et al., "Non-Restarting CUSUM charts and Control of the False Discovery Rate", Biometrika, (2013), 100 (1): 10 pages.
Sibanda, T. et al., "The CUSUM chart method as a tool for continuous monitoring of clinical outcomes using routinely collected data", BMC Medical Research Methodology, doi: 10.1186/1471-2288-7-46, 7(46) (2007): 7 pages.
Lau, F. et al., "Optimality of Non-Restarting CUSUM Charts." Sequential Analysis 32(4) (2013): 458-468.
Medicare Shared Savings Program (MSSP) ACO Quality Measures https://www.cms.gov/Medicare/Medicare-Fee-for-Service-Payment/sharedsavingsprogram/Downloads/2018-and-2019-quality-benchmarks-guidance.pdf (accessed on Jan. 31, 2019).
Thor, Johan, et al. "Application of statistical process control in healthcare improvement: systematic review." BMJ Quality & Safety in Health Care 16(5) (2007): 387-399.
Katz-Rogozhnikov, Dmitriy A., et al. "Toward Comprehensive Attribution of Healthcare Cost Changes." 2015 IEEE International Conference on Data Mining Workshops (ICDMW). IEEE (2015).
Keller, Deborah S., et al. "Initiating statistical process control to improve quality outcomes in colorectal surgery." Surgical endoscopy 29(12) (2015): 3559-3564.
Ray, Kristin N., et al. "Impact of Implementation of Electronically Transmitted Referrals on Pediatric Subspecialty Visit Attendance." Academic pediatrics 18(4) (2018): 409-417.

* cited by examiner

EXAMPLE OF CHANGE PATTERN CHARACTERIZATION: MULTI-RESOLUTION ANALYSIS

| CHANGE CHARACTERIZATION | RESULTS FROM SHORT-RUN HIGH-RESOLUTION ANALYSIS | RESULTS FROM LONG-RUN HIGH-RESOLUTION ANALYSIS |
|---|---|---|
| EMERGING GROWTH | INCREASE | NO CHANGE |
| EMERGING DECLINE | DECREASE | NO CHANGE |
| PERSISTENT GROWTH | INCREASE | INCREASE |
| PERSISTENT DECLINE | DECREASE | DECREASE |
| STABILIZING GROWTH | NO CHANGE | INCREASE |
| STABILIZING DECLINE | NO CHANGE | DECREASE |

FIG.21

SEARCHING AND DETECTING INTERPRETABLE CHANGES WITHIN A HIERARCHICAL HEALTHCARE DATA STRUCTURE IN A SYSTEMATIC AUTOMATED MANNER

1. Technical Field

Present invention embodiments relate to techniques for identifying relationships in complex, sparse data, and in particular, to using a hierarchical data structure to represent healthcare data, and to searching and identifying the hierarchical data to identify performance information.

2. Discussion of the Related Art

Healthcare cost is a growing financial burden in numerous economies. Accordingly, there is a strong interest in better understanding performance drivers of healthcare costs in a timely and specific manner. Cost-bearing entities, such as public agencies, private health plans, and self-insured employers, are particularly interested in identifying emerging cost patterns, including patterns that increase or decrease healthcare cost, in order to intervene or change policies to stabilize or reduce cost. However, emerging performance drivers are often insidious and hidden in large healthcare databases and/or pages of disparate summary reports.

Analysts or data scientists tasked with performance driver detection can be overwhelmed by finding actual performance drivers among millions of potential drivers, Additionally, analysts or data scientists may be influenced by personal or other types of bias and/or confused by nonstandard healthcare-specific terminologies present in healthcare data. Often, by the time performance driver detection is complete, millions of dollars have already been spent that might have been saved had the performance driver been detected in a timely manner.

SUMMARY

According to embodiments of the present invention, computer-implemented methods, systems, and computer readable media are provided for identifying and optimizing performance drivers of a healthcare related system. Healthcare related data may be analyzed to produce performance information pertaining to performance indicators for performance drivers of the healthcare related system, wherein the performance information includes plural sets of the performance indicators determined over time with each set associated with a corresponding performance driver, a corresponding path of a hierarchy of the performance drivers with parameters for aggregation of attributes, and a corresponding series of parameters for aggregating over time. From the performance information, changes in the sets of performance indicators over time for the performance drivers may be determined and performance drivers with determined changes satisfying a threshold may be identified.

An impact of the determined changes in the performance indicators to the identified performance drivers and contributions to the determined impact from one or more factors may be identified, wherein each factor is associated with utilization of one or more items by subjects.

Factors of the identified performance drivers with opposing utilization trends may be identified and an impact of the identified factors on the performance drivers may be determined based on migration of quantities of subjects between the factors with opposing utilization trends. The identified performance drivers may be ranked based on the impact of the determined changes and the impact of the identified factors. Use of the performance drivers may be adjusted based on the ranking to optimize performance of the healthcare related system.

It is to be understood that the Summary is not intended to identify key or essential features of embodiments of the present disclosure, nor is it intended to be used to limit the scope of the present disclosure. Other features of the present disclosure will become easily comprehensible through the description below.

BRIEF DESCRIPTION OF THE DRAWINGS

Generally, like reference numerals in the various figures are utilized to designate like components.

FIG. 21 shows examples of change patterns that may be characterized by rule-based techniques according to the results of multi-resolution analysis, according to embodiments of the present disclosure.

DETAILED DESCRIPTION

Methods, systems, and computer readable media are provided for identifying performance drivers of a healthcare related system with complex and hierarchical health data.

Healthcare data may be high dimensional and sparse, and therefore, searching the healthcare data space may result in performance drivers with varying signal strength. In addition, healthcare data capture can be inconsistent across sources, due to differences in coding practice, differences in data collection speed, or other factors.

Healthcare performance drivers also tend to be interrelated, making it difficult to isolate primary underlying performance drivers. For example, a cost increase in a particular geographical region can be due to a combination of performance drivers, such as changes in individual health status, provider practice patterns, treatment availability, type of treatment, etc. Healthcare performance drivers may also be influenced by seasonal or cyclical factors (e.g., due to influenza outbreaks which may primarily occur in). Other performance drivers may include behavioral changes in a patient or a provider. For example, patients may seek additional preventative services after a certain age (e.g., colonoscopy screenings, mammograms, etc.), or a provider may adhere to new clinical guidelines for treatment of a disease. Other performance drivers may include introduction, repurposing, or discontinuation of therapy options. Present invention embodiments allow for identification of performance drivers despite these aforementioned factors.

Figure 1:
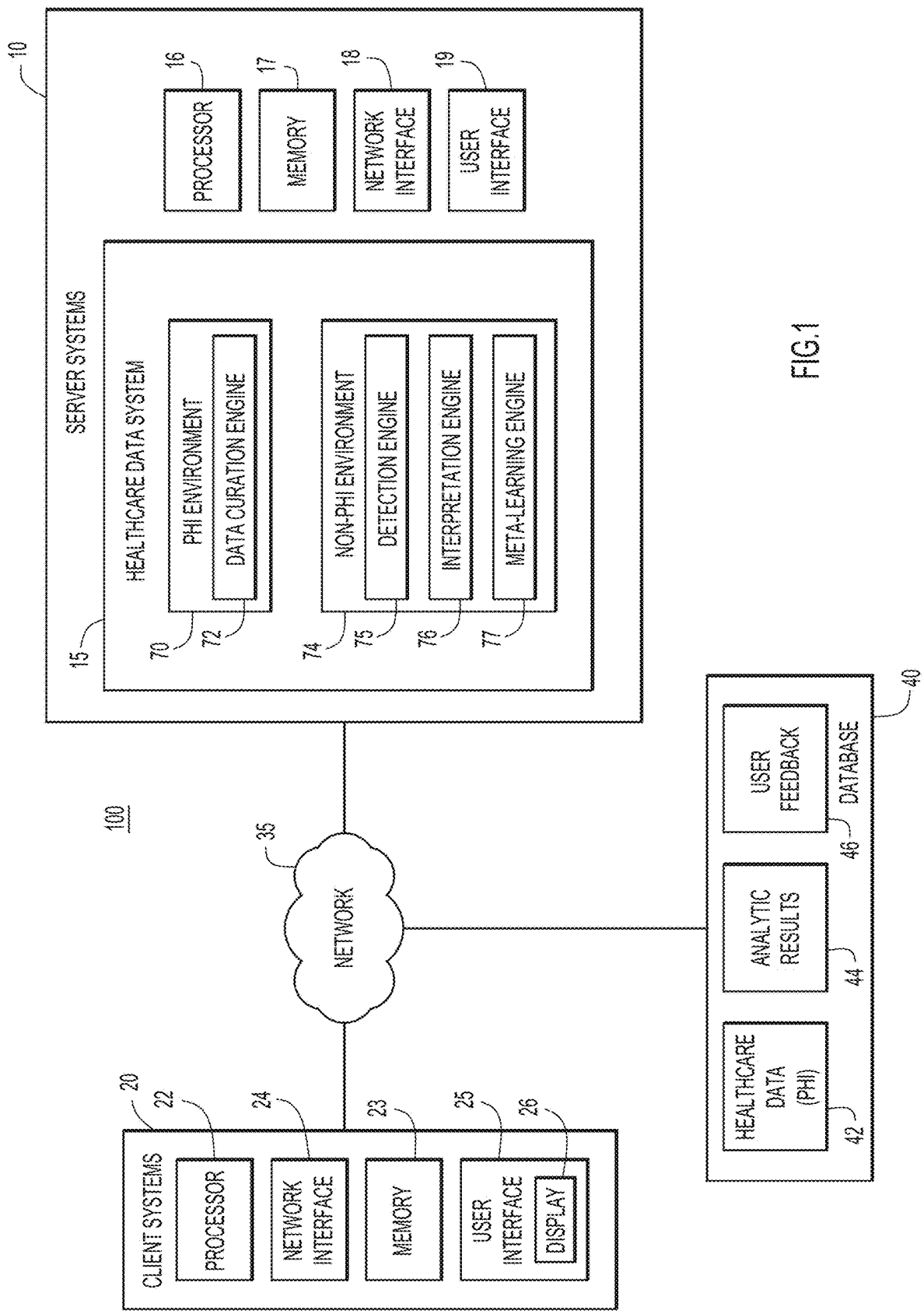
FIG. 1 is a block diagram of an example computing environment for the healthcare data system, according to embodiments of the present disclosure.

An example environment for use with present invention embodiments is illustrated in FIG. 1. Specifically, the environment includes one or more server systems 10, and one or more client or end-user systems 20. Server systems 10 and client systems 20 may be remote from each other and communicate over a network 35. The network may be implemented by any number of any suitable communications media (e.g., wide area network (WAN), local area network (LAN), Internet, Intranet, etc.), Alternatively, server systems 10 and client systems 20 may be local to each other, and may communicate via any appropriate local communication medium (e.g., local area network (LAN), hardwire, wireless link, Intranet, etc.).

Client systems 20 enable users to submit queries (e.g., containing performance information, etc.) to server systems 10 for analysis to identify performance drivers, and may provide reports to users regarding the identified performance drivers or may provide a user-interface with which a user may interact to traverse a hierarchical healthcare data system in order to obtain information regarding specific performance drivers. Hierarchies may be constructed based on domain knowledge, Drivers may be related to each other, and may be represented with a hierarchical structure.

A database system 40 may store various information for the analysis (e.g., healthcare data 42, which may be hierarchical, analytic results 44, user feedback 46, etc.). The database system may be implemented by any conventional or other database or storage unit, may be local to or remote from server systems 10 and client systems 20, and may communicate via any appropriate communication medium (e.g., local area network (LAN), wide area network (WAN), Internet, hardwire, wireless link, Intranet, etc.). The client systems may present a graphical user (e.g., GUI, etc.) or other interface (e.g., command line prompts, menu screens, etc.) to solicit information from users pertaining to the desired documents (e.g., insurance claims, medical summaries or reports, etc.) and analysis, and may provide reports including analysis results (e.g., list of identified performance drivers, which may be ranked, etc.).

Server systems 10 and client systems 20 may be implemented by any conventional or other computer systems preferably equipped with a display or monitor, a base (e.g., including at least one processor 16, 22, one or more memories 17, 23 and/or internal or external network interfaces or communications devices 18, 24 (e.g., modem, network cards, etc.)), optional input devices (e.g., a keyboard, mouse or other input device), user interface 19, 25 (with a display 26), and any commercially available and custom software (e.g., server/communications software, healthcare data system 15 including Protected Health Information (PHI) environment 70 and non-PHI environment 74, browser/interface software, etc.).

Alternatively, one or more client systems 20 may query a hierarchical healthcare data system to identify performance drivers by the healthcare data system 15 when operating as a stand-alone unit. In a stand-alone mode of operation, the client system stores or has access to the data (e.g., healthcare data 42, etc.), and includes a healthcare data system 15. The graphical user (e.g., GUI, etc.) or other interface (e.g., command line prompts, menu screens, etc.) solicits information from a corresponding user pertaining to the desired documents (e.g., insurance claims, medical summaries or reports, etc.) and analysis, and may provide reports including analysis results (e.g., list of identified performance drivers, which may be ranked, etc.).

Healthcare data system 15 may include one or more modules or units to perform the various functions of present invention embodiments described herein. The various modules (e.g., PHI environment 70, non-PHI environment 74, etc.) may be implemented by any combination of any quantity of software and/or hardware modules or units, and may reside within memory 17, 23 of the server and/or client systems for execution by processor 16, 22.

PHI environment 70 stores healthcare input data for analysis by the non-PHI environment. The PHI environment 70 may comprise data curation module 72 for preparing and processing healthcare input data (e.g., claims, medical summaries, etc.) and features (drivers) per healthcare hierarchy, as well as preparing summarized healthcare data inputs for subsequent processing in the non-PHI environment 74. Data aggregation may occur in the PHI environment.

The non-PHI environment 74 detects performance driver changes over time, interprets the results to identify performance drivers, captures user feedback regarding performance drivers, and learns over time from user feedback, machine learning, and data analytics. The engines (e.g., detection engine 75, interpretation engine 76, and meta-learning engine 77, etc.) are deployed in a privacy-protected manner, providing additional flexibility in software deployment environments and reducing the difficulty of sharing results among users as well as facilitating learning from an aggregated data set.

Accordingly, data curation is performed on information containing PHI in the PHI environment, and the curated data is deployed to a non-PHI environment in a manner that protect privacy while allowing searching, detection, and learning from the non-PHI data. This type of implementation provides additional flexibility in software deployment environments for core analytic engines (e.g., data curation engine 72, detection engine 75, interpretation engine 76, and meta-learning engine 77, etc.) and reduces potential barriers from cross-user result sharing and learning from aggregated data.

Detection engine 75 may mine millions of performance drivers in healthcare data 42, in a systematic and intelligent manner, e.g., using hots to analyze data. Detection engine may search aggregated data in a hierarchical structure to detect changes, e.g., fir each KPI. Interpretation engine 76 ingests detected performance drivers, interprets the performance drivers within a healthcare context, and identifies surface "themes". The interpretation engine may gather user feedback via user interface 25 and may store the gathered data in analytic results 44 and/or user feedback 46 in a database, which may be provided to meta-learning engine 77. Once changes are detected, the interpretation engine may seek to understand such changes, e.g., for example, whether the change is a persistent change, reverse trend, new trend, etc. Meta learning engine 77 may comprise a machine learning module to learn from data updates and user feedback to improve interpretation, e.g., to include rankings. These engines are described in additional detail below.

With reference to the following figures and description, an event may correspond to an episode; a user may correspond to a patient or claimant; a membership may correspond to an enrollee; a performance score may correspond to a cost; and a viewpoint may correspond to a drill path in a healthcare data hierarchy.

Figure 2:
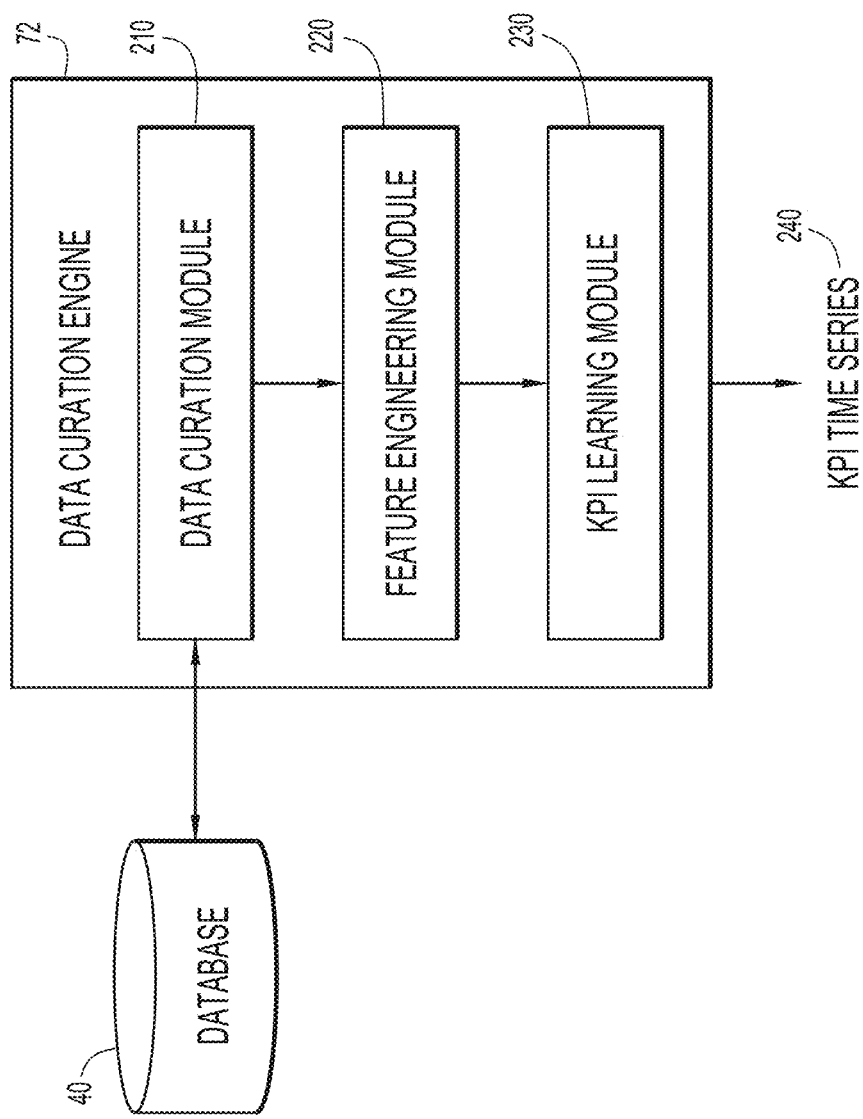
FIG. 2 is a block diagram of the components of a data curation engine, according to embodiments of the present disclosure.

FIG. 2 is a block diagram of the components of a data curation engine 72. Data curation engine 72 may comprise data curation module 210, feature engineering module 220, and key performance indicator (KPI) learning module 230. Data curation module may analyze data within specified time windows (e.g., 3 months, 6 months, 12 months, etc.). For example, a user may specify a window of time in which to analyze data (see, e.g., FIG. 18). In some aspects, performance indicators are entities/attributes that impact performance drivers, such as cost, quality, etc. A driver may be impacted by a combination of attributes.

In some aspects, an event label may be assigned to data records in order to group the data records based on the assigned event label. Attributes of the data records may be mapped to the hierarchy of medical data.

Data curation module 210 may interface with database 40 to obtain information pertaining to a query. In some aspects, a query may be provided by a user, wherein the query relates to a performance driver. In some aspects, a time analysis window is provided, e.g., by a user or in an automated manner, which sets a time period over which to select and analyze pertinent data. The selected data may be organized based on specific comparative time windows, and provided to feature engineering module 220.

Feature engineering module 220 may generate reference or mapping files, to map performance drivers to specific categories of performance indicators, and may receive information from data curation module 210. Attributes of the data records may be mapped to the hierarchy of medical data.

Figure 3:
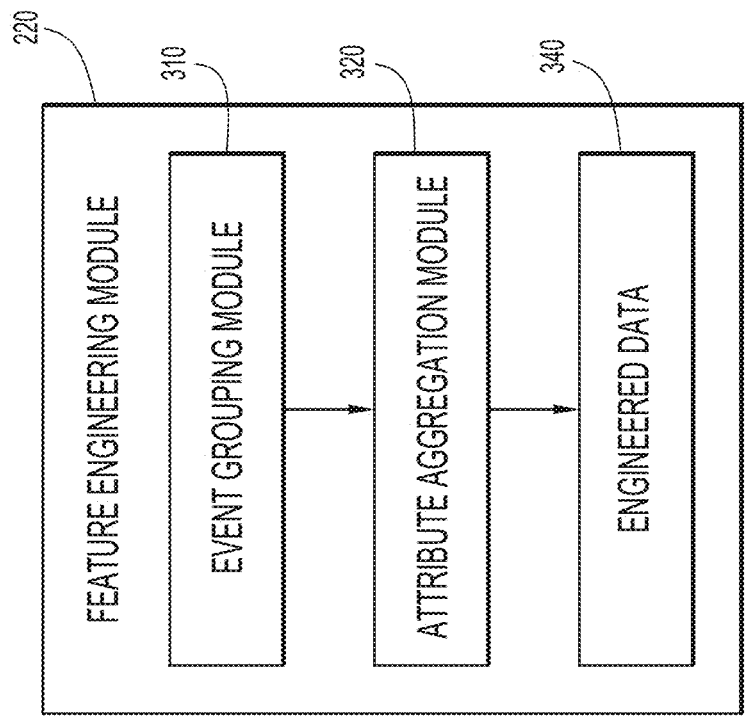
FIG. 3 is a block diagram of the components of a feature engineering module, according to embodiments of the present disclosure.

As shown in FIG. 3, feature engineering module 220 may comprise an event grouping module 310 and an attribute aggregation module 320. Event grouping module 310 may group disparate data records into meaningful clinical events by assigning an event label (e.g., treatment episodes, admissions) to each record. Event grouping logic and/or event labels may be provided to group data records based on one or more labels. The grouped information is provided to attribute aggregation module 320, which maps values of some or all data attributes according to hierarchical clinical concepts to produce engineered data 340. The engineered data may be provided to KPI learning module 230.

KPI learning module 230 may aggregate data in different manners, including time period-based aggregation of data or attribute-based aggregation of data. In some aspects, a viewpoint of the healthcare data hierarchy may be defined, e.g., in an automated manner or by a user, to enable attribute-based aggregation of data. The data curation engine 72 may output IPI time series 240, based on performance drivers, a hierarchical viewpoint, and analysis type.

KPI learning module 230 receives engineered data from feature engineering module 220. The KPI learning module may comprise a KPI calculator which performs various types of analysis on the engineered data. For this analysis, the following parameters may be provided. For time-based aggregation, a time horizon may be specified, indicating the number of analysis time windows to be used. A resolution may be provided, which corresponds to a length of a period of time as a fraction of an analysis time window. For attribute-based aggregation, a set of features may be provided to group the data records, wherein each combination of the feature values is referred to as a driver.

The output of the KPI calculator may be provided as a KPI time series including drivers, hierarchical viewpoint, and analysis type. The KPI time series may include, but is not limited to, the following parameters: event counts, user counts, membership counts, event to membership ratio (EMR), user to membership ratio (UMR), event to user ratio (EUR), average performance score per event, and standard error of performance score per event.

Figure 4:
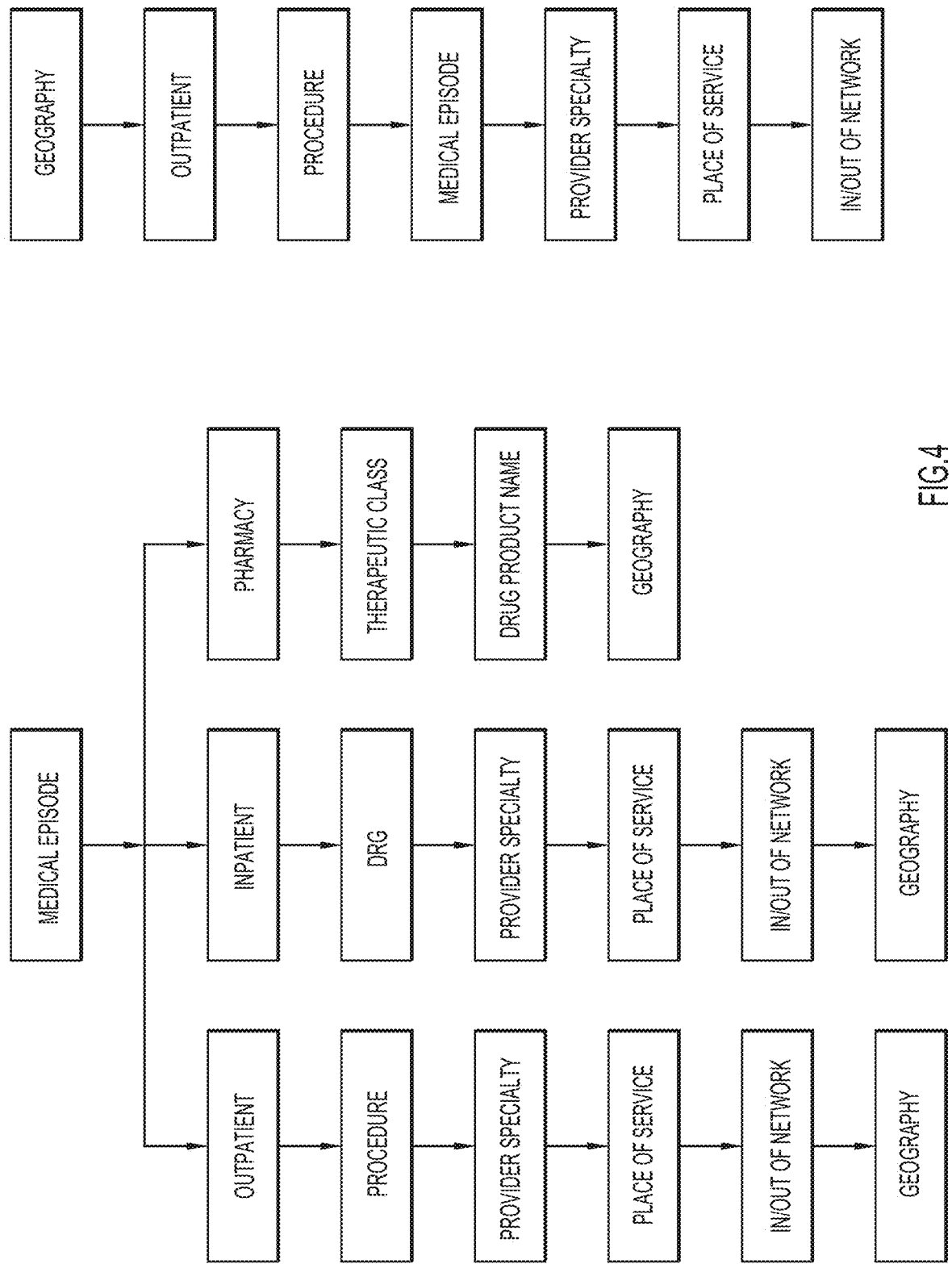
FIG. 4 is an example viewpoint hierarchy for healthcare data, according to embodiments of the present disclosure.

FIG. 4 is an example viewpoint hierarchy for healthcare data. Utilizing a hierarchical search strategy allows the system to leverage domain-knowledge-based attribute hierarchies (trees) to search for impactful performance drivers.

In this example, different hierarchies are possible for a set of events. For example, medical episode may be at the top of one viewpoint hierarchy but in the middle of another viewpoint hierarchy (geography). A hierarchy offers different levels of grouping based on insurance claim reports and other medical information. For example, a first level may encompass a type of visit (e.g., outpatient, inpatient, or pharmacy visit). Drilling down a path of the hierarchy may include different events in a specified order (e.g., procedure, provider specialty, place of service, etc.). In some aspects, the hierarchies may be customized to answer specific medical questions about performance drivers, including cost. For example, if costs have escalated at one medical facility (place of service) but not others, the hierarchy may be configured to analyze data from this medical facility in order to identify cost drivers specific to this facility.

Figure 5:
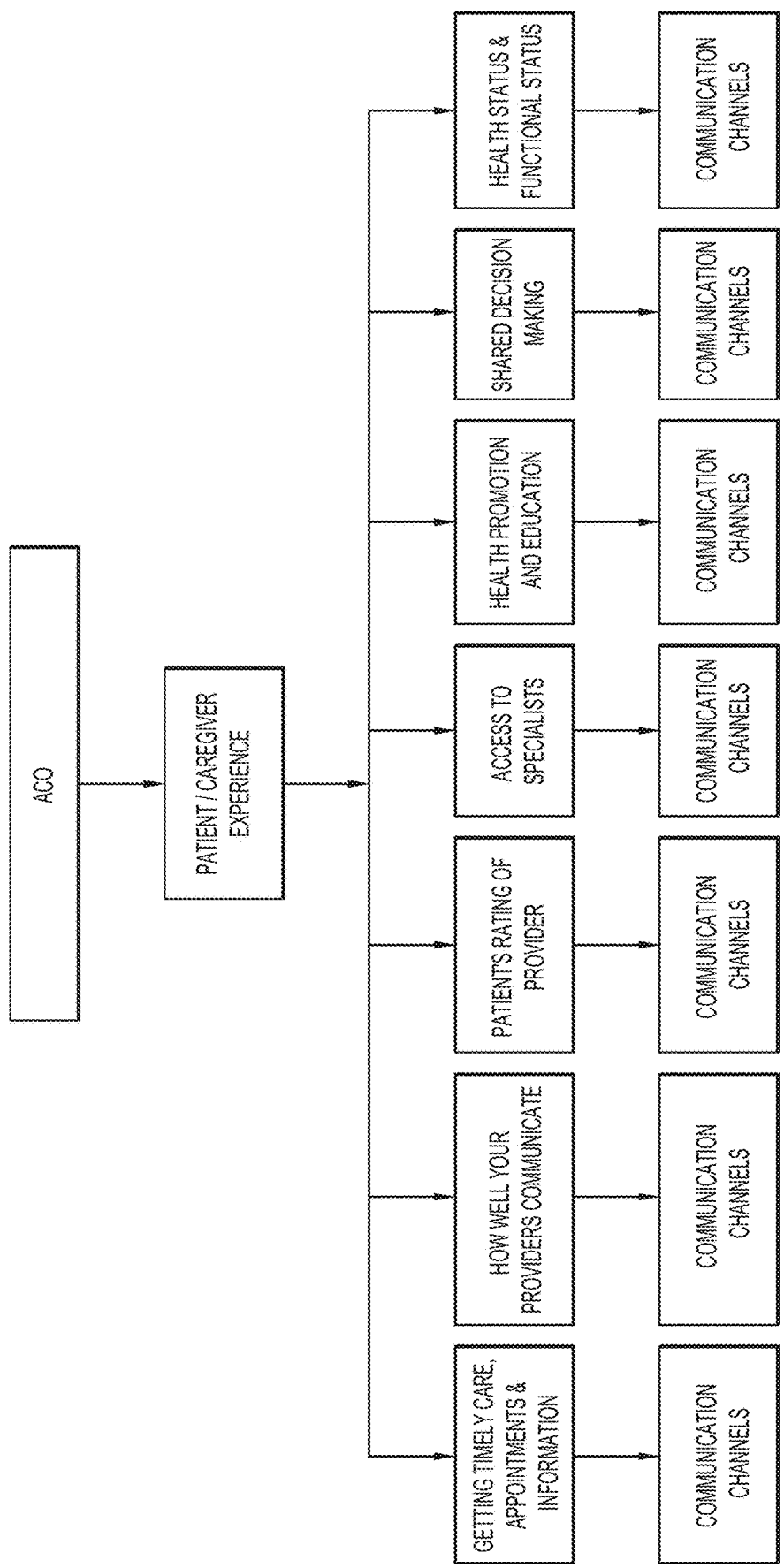
FIG. 5 is another example of a viewpoint hierarchy for patient satisfaction, according to embodiments of the present disclosure.

FIG. 5 is another example of a viewpoint hierarchy. In this example, the hierarchy is tailored to Consumer Assessment of Healthcare Providers and Systems (CAHPS) Survey for Accountable Care Organizations (ACCs) Quality Measures to assess patient satisfaction at particular facilities. This hierarchy is generated based on user surveys, usually obtained at respective doctor's visit. Various viewpoints may include visit type (inpatient vs. outpatient), medical conditions, medical treatments, provider specialty, and communication channels.

ACO Quality Measures may include but are not limited to an event (e.g., visit), user (e.g., patient respondents), membership (e.g., Medicare beneficiary assigned to ACO), and performance score (e.g., quality score).

Various metrics may be computed including KPI time series by drivers, viewpoint hierarchy, and analysis type, including event counts (e.g. number of visits), user counts (e.g. number of patients), membership counts (e.g. number of ACO beneficiaries), event to membership ratio (EMR) (e.g., visits to beneficiary ratio), user to membership ratio (UMR) (e.g., patient to beneficiary ratio), event to user ratio (EUI) (e.g., visit to patient ratio), average performance score per event (e.g., quality score per doctor), and standard error of performance score per event.

In this example, sets of performance indicators are provided with each set associated with a corresponding performance driver. For example, for a driver that is patient experience, performance indicators may include but are not limited to timely care, provider's rating, access to specialists, provider communication, etc.

Figure 6:
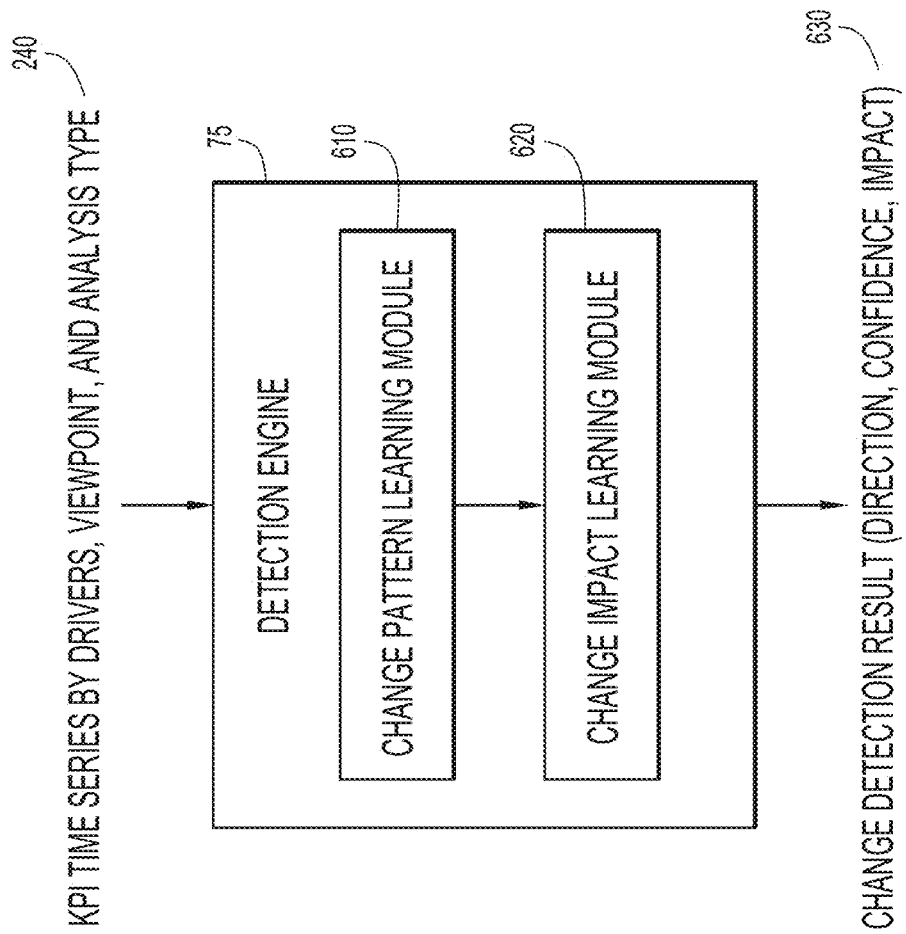
FIG. 6 is a block diagram showing components of a detection engine, according to embodiments of the present disclosure.
Figure 7A:
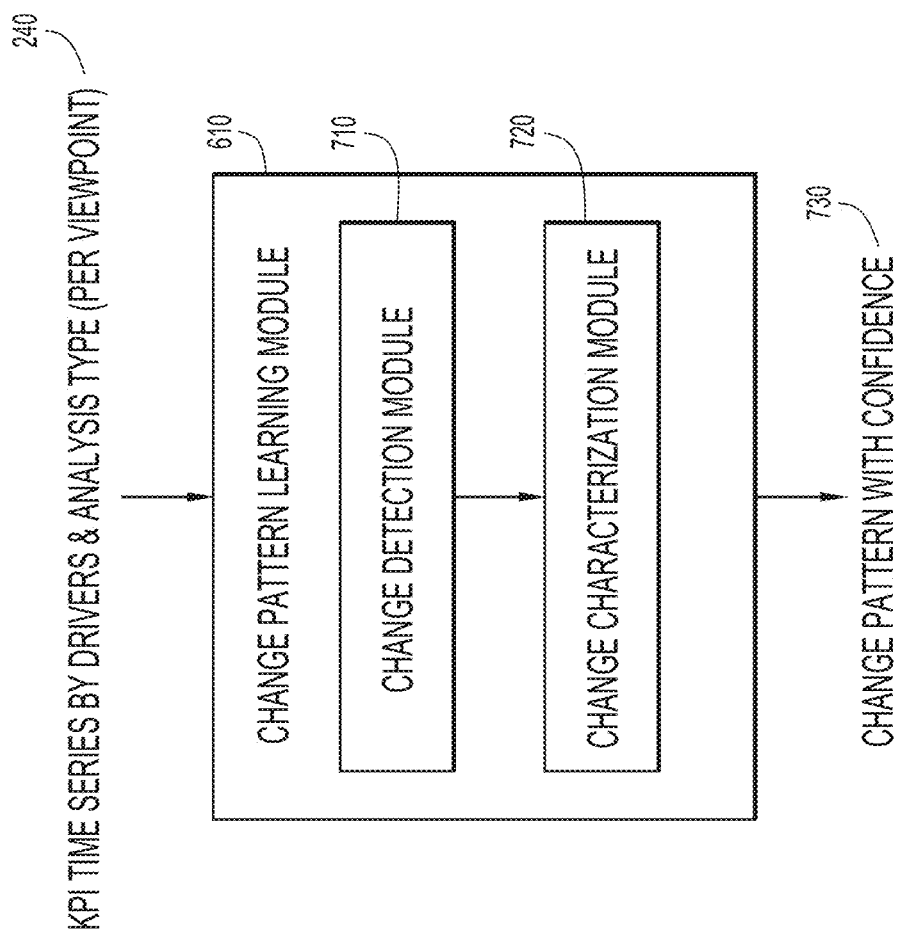
FIG. 7A is a block diagram showing a change pattern learning module, according to embodiments of the present disclosure.

FIG. 6 is a block diagram showing components of detection engine 75, including change pattern learning module 610 and change impact learning module 620. Control parameters may be provided, either by a user or as preset parameters, to each module. KPI time series data 240 (grouped by drivers, viewpoint, and/or analysis type) may be provided to detection engine 75 for further analysis. The output of the detection engine may include change detection results 630, which includes a direction of change, a statistical confidence, and impact that may correspond to a monetary or other value). Each module is described in additional detail below, FIG. 7A is a block diagram showing change pattern learning module 610, which may comprise change detection module 710 and change characterization module 720. Change detection module 710 may detect the presence of a significant change. Change characterization module 720 may profile the detected change. Change pattern learning module may receive as input a KPI time series, and may produce as output, a change pattern 730 identified with confidence.

In some aspects, changes may be classified into change patterns, e.g., based on a threshold determined by a machine learning model. In some aspects, a change pattern may comprise a direction of change (e.g., increasing, decreasing, staying about the same) and a rate of change.

Figure 7B:
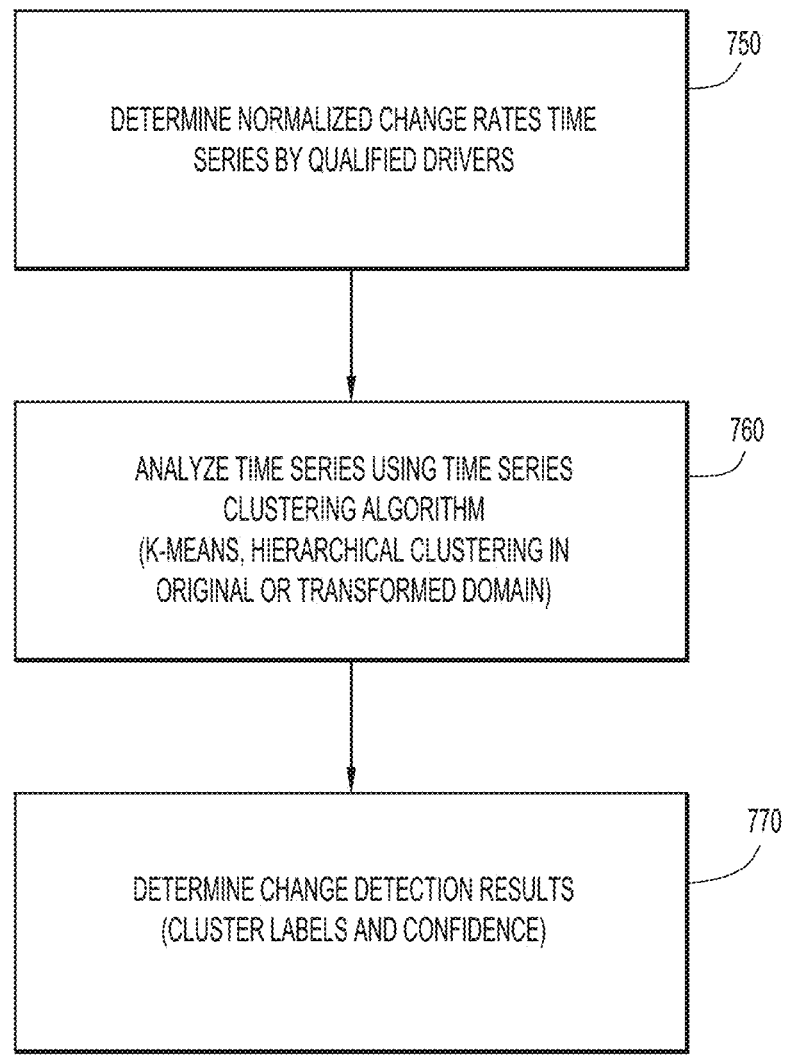
FIG. 7B is a flowchart showing an alternative implementation of a change pattern learning module, according to embodiments of the present disclosure.

FIG. 7B is a flowchart showing an alternative implementation of change pattern learning module 610. At operation 750, normalized change rates time series by qualified drivers are determined. At operation 760, a time series clustering algorithm (K-means, hierarchical clustering in original or transformed domain) is utilized. At operation 770, change detection results (e.g., cluster labels and confidence) are determined.

Figure 8A:
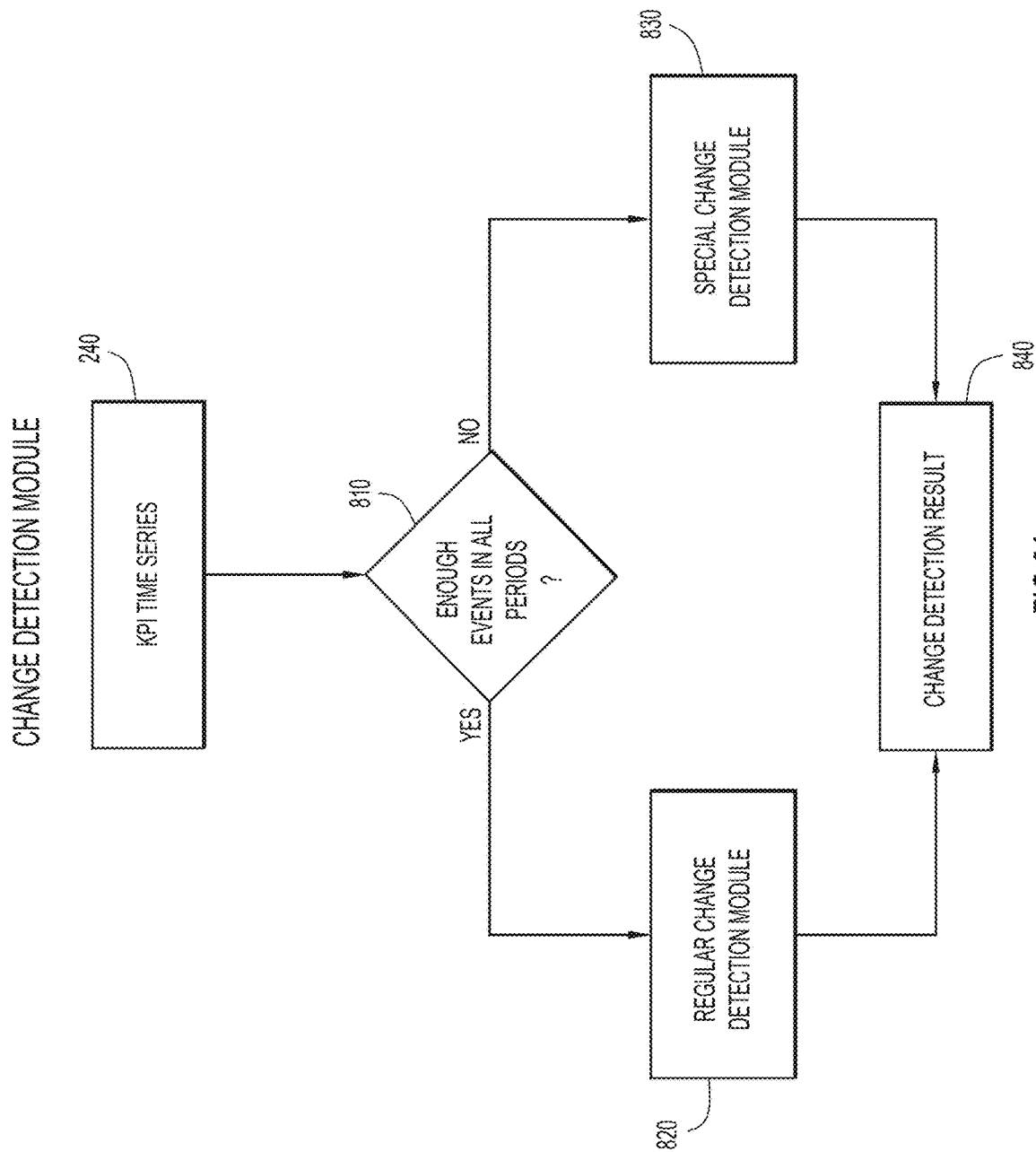
FIG. 8A is an operational flowchart of a change detection module, according to embodiments of the present disclosure.

FIG. 8A is an operational flowchart of the change detection module. At operation 810, for each analysis type, KPI time series 240 is analyzed to determine whether there are enough events in all periods. In some aspects, determination is based on a detection threshold designed to address data sparsity, e.g., a pre-defined threshold derived from historic data to delineate drivers by data volume. If there are enough events, at operation 820, analysis may proceed according, to regular change detection module 820. If there are not enough events, at operation 830, analysis may proceed according to special change detection module 830, which compensates for sparse data. At operation 840, change detection result 840 is produced by change detection module 820/830.

Figure 8B:
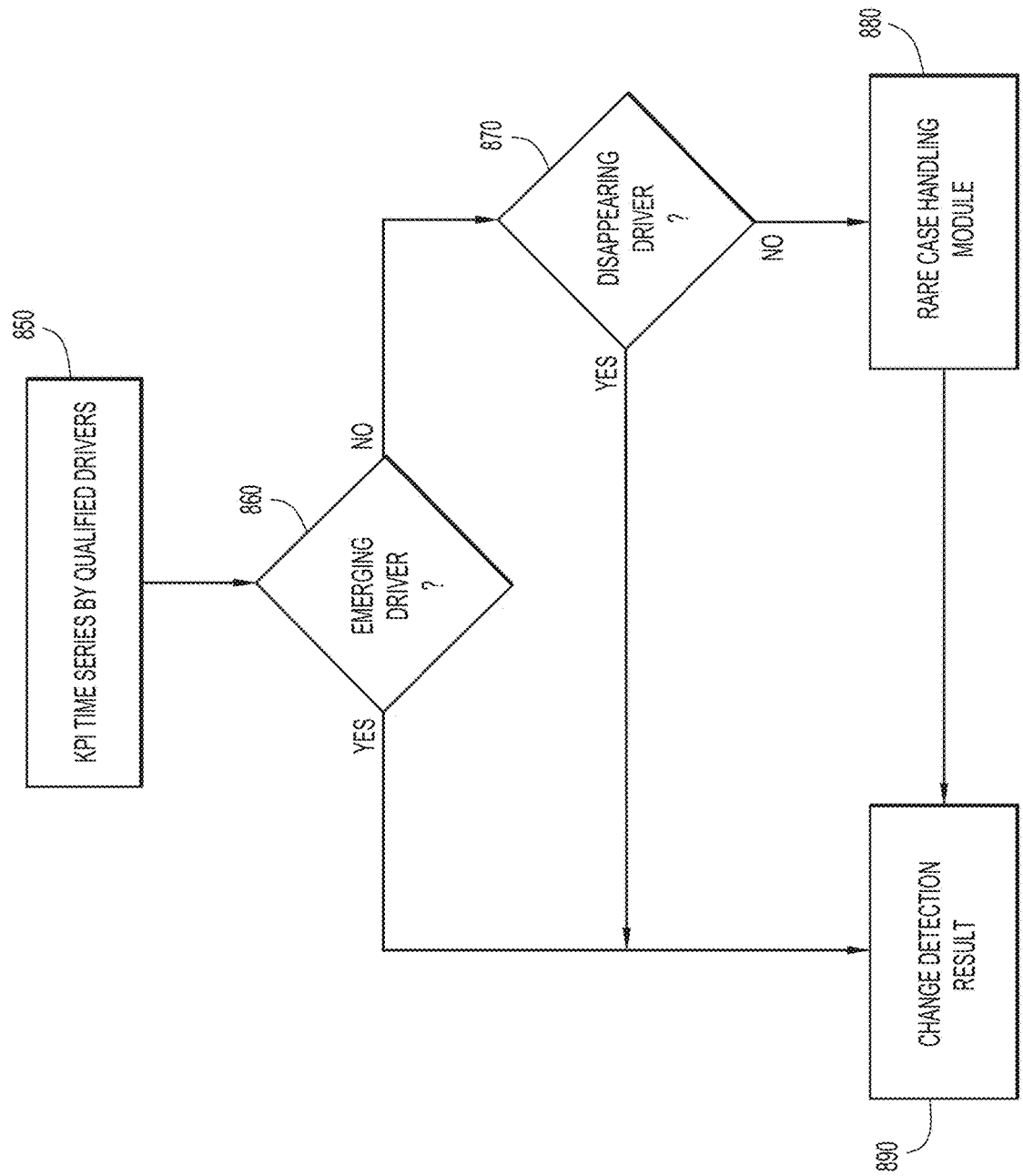
FIG. 8B is an operational flowchart of a special change detection module, according to embodiments of the present disclosure.

FIG. 8B is an operational flowchart of a special change detection module, according to embodiments of the present disclosure. At operation 850, a KM Time Series by qualified drivers is provided. At operation 860, the system evaluates the KPI time series for the presence of an emerging driver. If an emerging driver is identified, change detection results are reported at operation 890. If an emerging driver is not identified, at operation 870, the system evaluates the KPI time series for the presence of a disappearing driver. If a disappearing driver is found at operation 870, change detection results are reported at operation 890. If a disappearing driver is not found, at operation 870, the KPI time series may be analyzed by a rare case handling module at operation 880, and change detection results may be reported at operation 890. In some aspects, rare case handling module may operate according to rules-based techniques. Detection thresholds may be provided for operations 860 and 870.

Figure 9A:
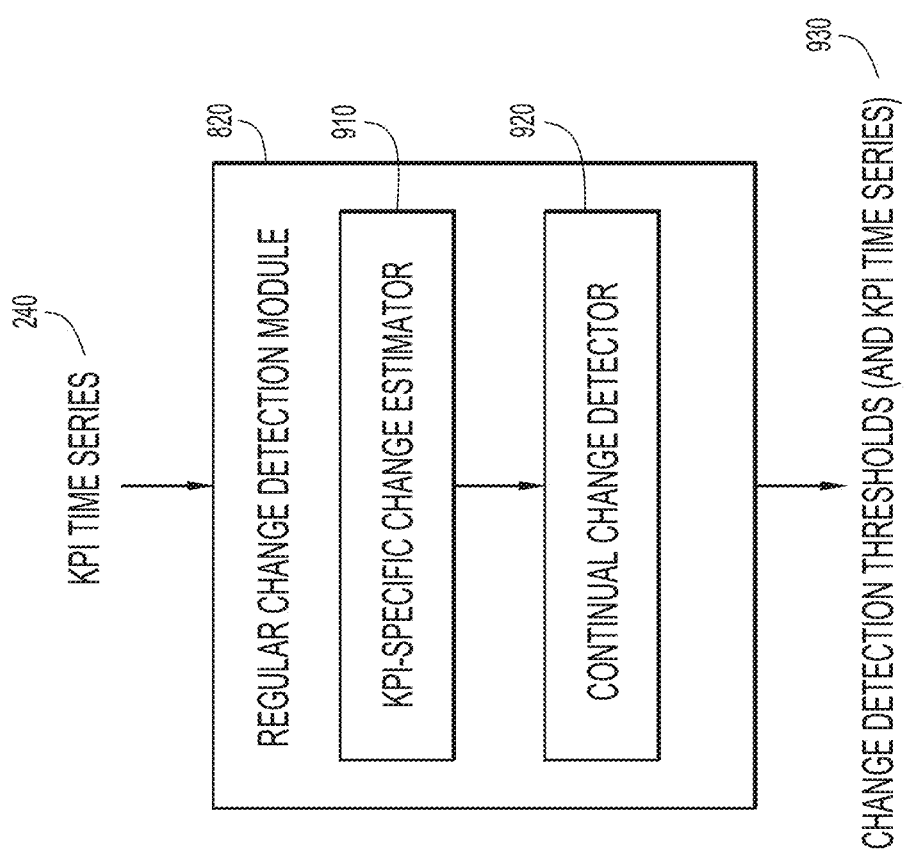
FIG. 9A is a block diagram of a regular change detection module, according to embodiments of the present disclosure.

FIG. 9A is a block diagram of regular change detection module 820. This module accepts KPI time series 240 data (by qualified drivers) as input. The KPI time series information 240 is analyzed by KPI-specific change estimator 910, which calculates a rate of change of a performance indicator as a function of time, and standardizes the change with a KPI-dependent normalizer. In some cases, regular change detection module 820 may analyze short and long range KPI data to detect short and long term changes.

KPI Time series also may be analyzed by continual change detector 920, which has three primary functionalities, including using a threshold learning module to establish a detection threshold through historical data modeling; using an online detection mechanism (e.g., using auto-reset or non-restarting CUSUM); and changing reporting rules (e.g., report changes at any point within the analysis window, or only report at the end of the analysis to focus on the latest cumulative effect of change).

KPI data may be analyzed by continual change detector 920, which uses a time series simulator comprising a statistical model of normalized rate of change time series (e.g., ARMA, Gaussian white noise, etc.). For each value in the set of trial thresholds, the continual change detector 920 processes each simulated time series, and the fraction of detected cases (false alarm rate) is computed and provided as output together with the threshold value. Trial thresholds may be provided by the user (e.g., based on historical information). This output is analyzed, and the threshold whose false alarm rate is closest to the target false alarm rate is identified. A target false alarm rate may be set by a user. A set of trial thresholds may be set by a user or may be predetermined. The regular change detection module 820 provides change detection thresholds 930 as output.

Figure 9B:
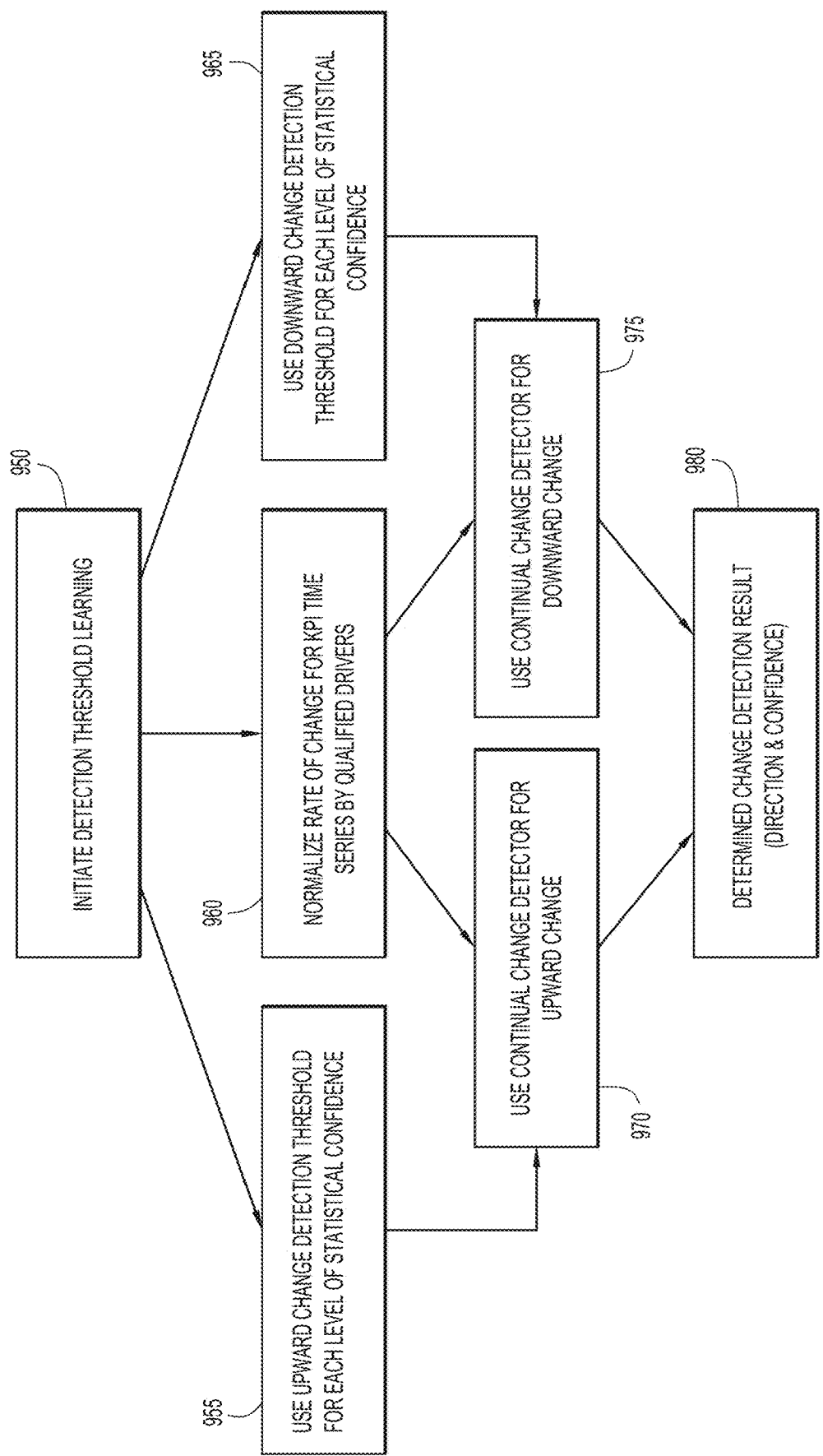
FIG. 9B is a flow chart showing operations of detection threshold learning, according to embodiments of the present disclosure.

FIG. 9B is a flow chart showing operations of detection threshold learning. At operation 950, detection threshold learning is initiated. At operation 955, an upward change detection threshold is used for each level of statistical confidence. At operation 960, the rate of change for a KPI time series is normalized. At operation 965, a downward change detection threshold is used for each level of statistical confidence. At operation 970, a continual change detector is used to detect upward change. At operation 975, a continual change detector is used to detect downward change. At operation 980, change detection results (with direction and confidence) are determined.

Figure 10:
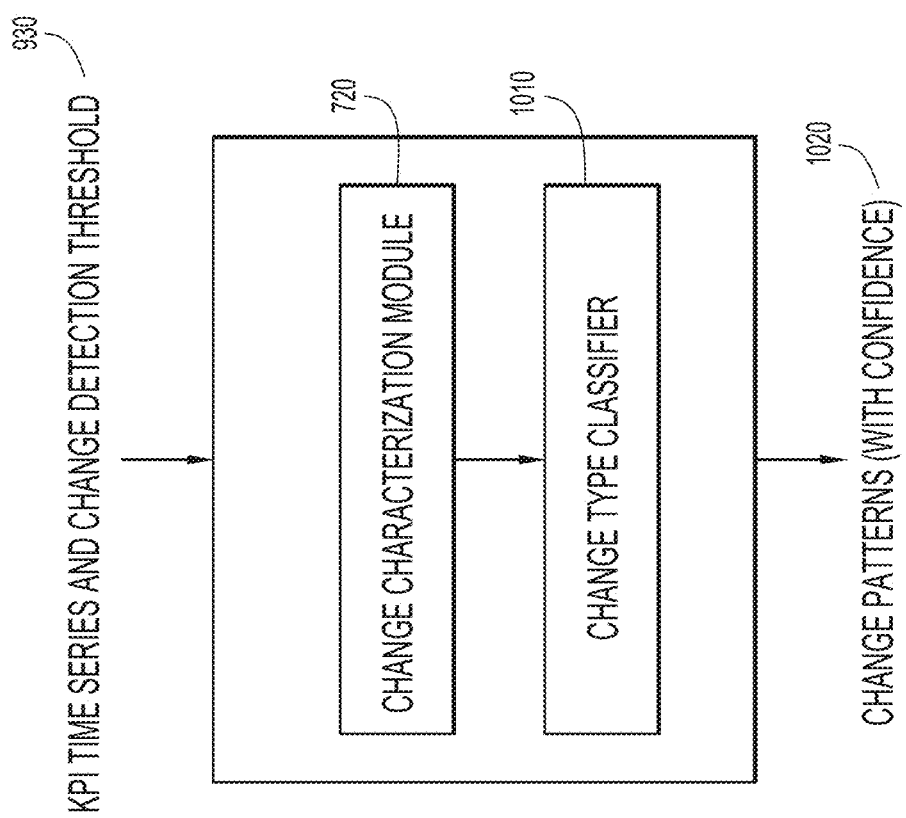
FIG. 10 is a block diagram of a change characterization module, according to embodiments of the present disclosure.

FIG. 10 is a block diagram of the change characterization module 720, which may receive KPI time series data and change detection thresholds by run type with confidence, for each detected driver. Change characterization module 720 may contain a change type classifier 1010, which classifies results from various analysis types into a change profile. The change characterization module turns KPI time series into interpretable features, e.g., persistent growth (slow rise over time), emerging decline (sharp drop after slow decline). To characterize KPI data, supervised machine learning classifiers (e.g., rules-based, neural net, etc.) or unsupervised classifiers (e.g., clustering, etc.) may be used. Change characterization module 720 generates change patterns with confidence 1020.

Figure 11:
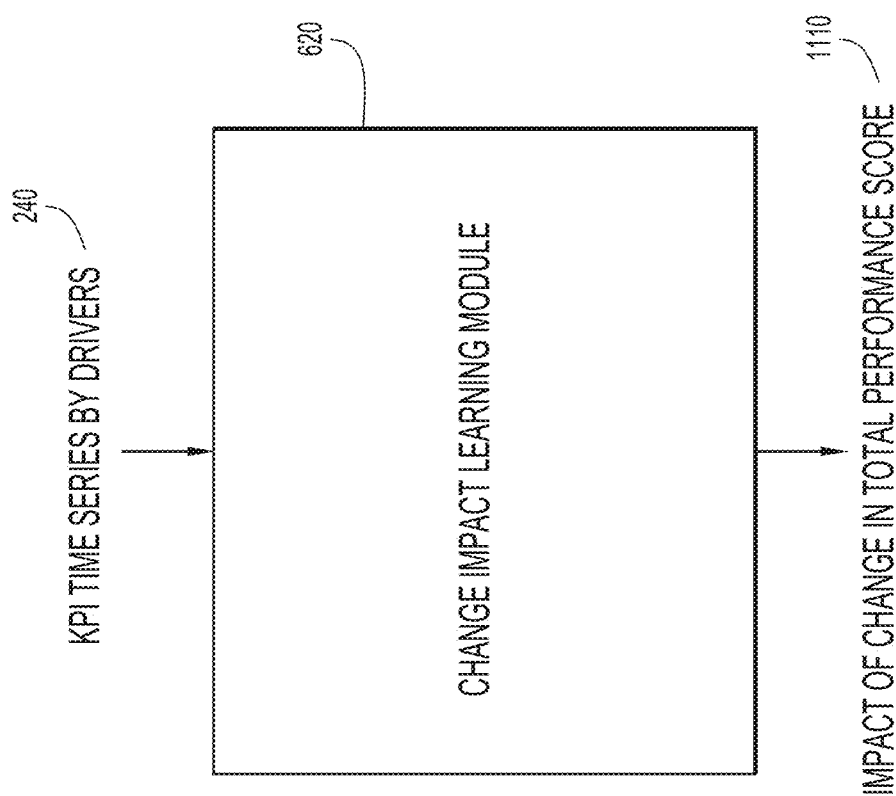
FIG. 11 is a flowchart of a change impact learning module, according to embodiments of the present disclosure.

FIG. 11 is a flowchart of change impact learning module 620. This module assesses the impact of change in a total performance score. The impact may be decomposed into an average performance score and utilization, and the utilization may be further decomposed into participation and frequency. Thus, the impact of change in the total performance score 1110 may be assessed in terms of the impact of change due to average performance score and impact of change due to utilization (EMR), and the impact of change due to utilization may be divided into the impact of change due to participation (UMR) and frequency (EUR).

The impact of change in total performance score may be determined by equation 1:

$$c(t)=s(t-T), t=T+1, \ldots, P$$

$$I(c)=EWA(c(T+1), \ldots, c(P)) \quad (1)$$

wherein s(t)=total performance score in period t, and wherein the exponentially weighted average (EWA) is $$\frac{1-w}{1-w^{P-T}} \sum_{t=T+1}^{P} w^{P-1} c(t) \quad (2)$$

The decomposition of impact due to participation by average performance score and utilization may be represented by the following set of equations:

$$c_1(t) = e(t-T)[a(t) - a(t-T)], t = T+1, \ldots, P \quad (3)$$
$$J(c_1) = EWA(c_1(T+1), \ldots, c_1(P))$$
$$c_2(t) = [e(t) - e(t-T)]a(t-T), t = T+1, \ldots, P$$
$$J(c_2) = EWA(c_2(T+1), \ldots, c_2(P))$$
$$\delta_1 = [J(c_1) + J(c_2)] - I(c)$$

wherein e(t)=event count in period t
and a(t)=average performance score per event in period t The impact of change due to average performance score may be represented by the following equation:

$$I(c_1) = J(c_1) - \delta_1 \times |J(c_1)|/[|J(c_1)| + |J(c_2)|] \quad (4)$$

The impact of change due to utilization (EMR) may be represented by:

$$I(c_2) = J(c_2) - \delta_1 \times |J(c_2)|/[|J(c_1)| + |J(c_2)|] \quad (5)$$

The decomposition of impact due to utilization by participation and frequency may be represented by the following set of equations:

$$c_3(t) = [u(t) - u(t-T)]f(t-T)a(t-T), t = T+1, \ldots, P \quad (6)$$
$$J(c_3) = EWA(c_3(T+1), \ldots, c_3(P))$$
$$c_4(t) = u(t-T)[f(t) - f(t-T)]a(t-T), t = T+1, \ldots, P$$
$$J(c_4) = EWA(c_4(T+1), \ldots, c_4(P))$$
$$\delta_2 = [J(c_3) + J(c_4)] - I(c_2)$$

wherein u(t)=user to membership ratio (UMR) in period t, and
f(t)=event to user ratio (EUR) in period t.
wherein the impact of change due to participation (UMR) is represented by the following equation:

$$I(c_3) = J(c_3) - \delta_2 \times |J(c_3)|/[|J(c_3)| + |J(c_4)|] \quad (7)$$

and the impact of change due to frequency (EUR) is represented by $$I(c_4) = J(c_4) - \delta_2 \times |J(c_4)|/[|J(c_3)| + |J(c_4)|]. \quad (8)$$

Figure 12:
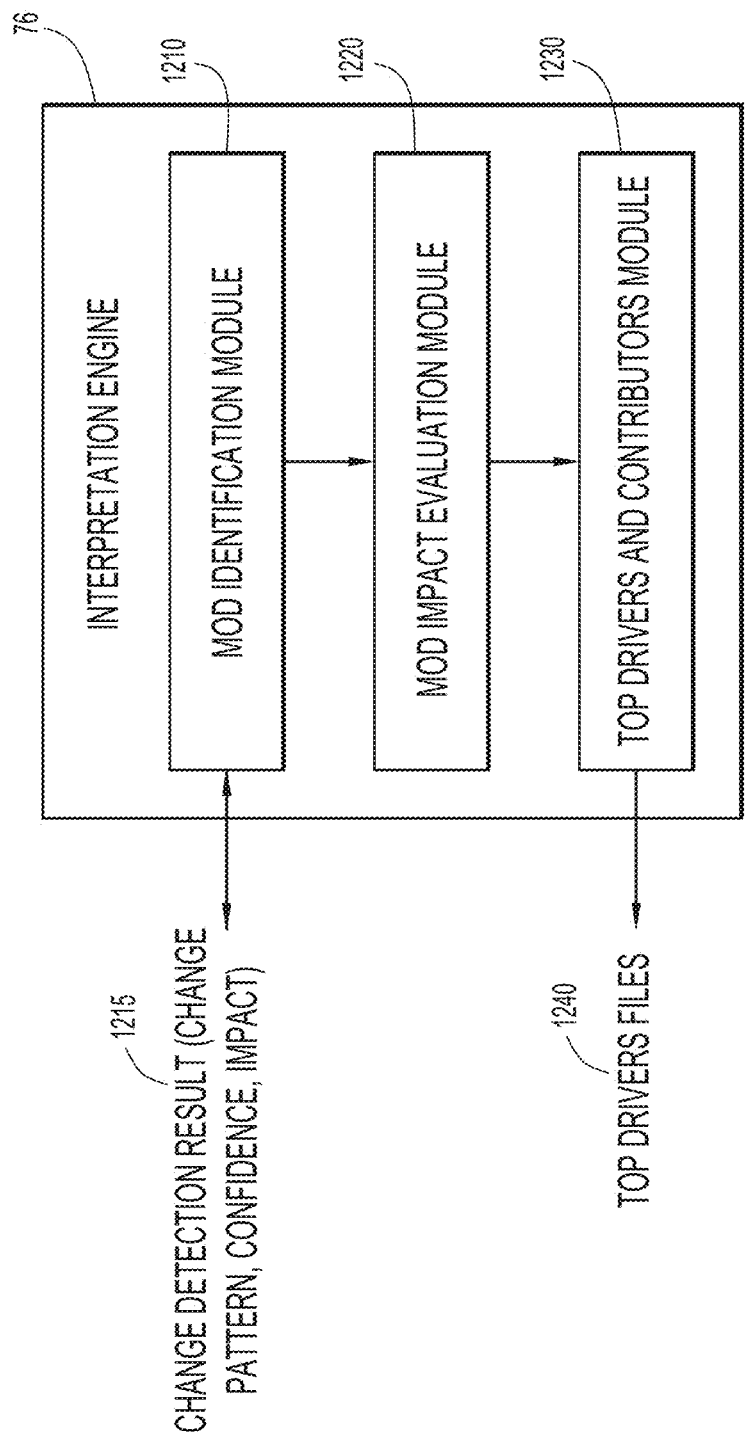
FIG. 12 is a block diagram of an interpretation engine, according to embodiments of the present disclosure.

FIG. 12 is a block diagram of interpretation engine 76. Interpretation engine 76 may comprise moving in opposite direction (MOD) identification module 1210, MOD impact evaluation module 1220, and top drivers and contributors module 1230. MOD identification module may include a knowledge base mapping, e.g., drug comparative effectiveness reference, drug mapping reference, etc., and may produce results corresponding to change detection (e.g., change pattern, confidence, impact, etc.). MOD impact evaluation module 1220 may receive KPI time series files for analysis. Top drivers and contributors module 1230 may receive control parameters for the analysis. The output of the system may include files or other outputs listing top performance drivers 1240. Each of these modules are described in additional detail as follows.

Figure 13:
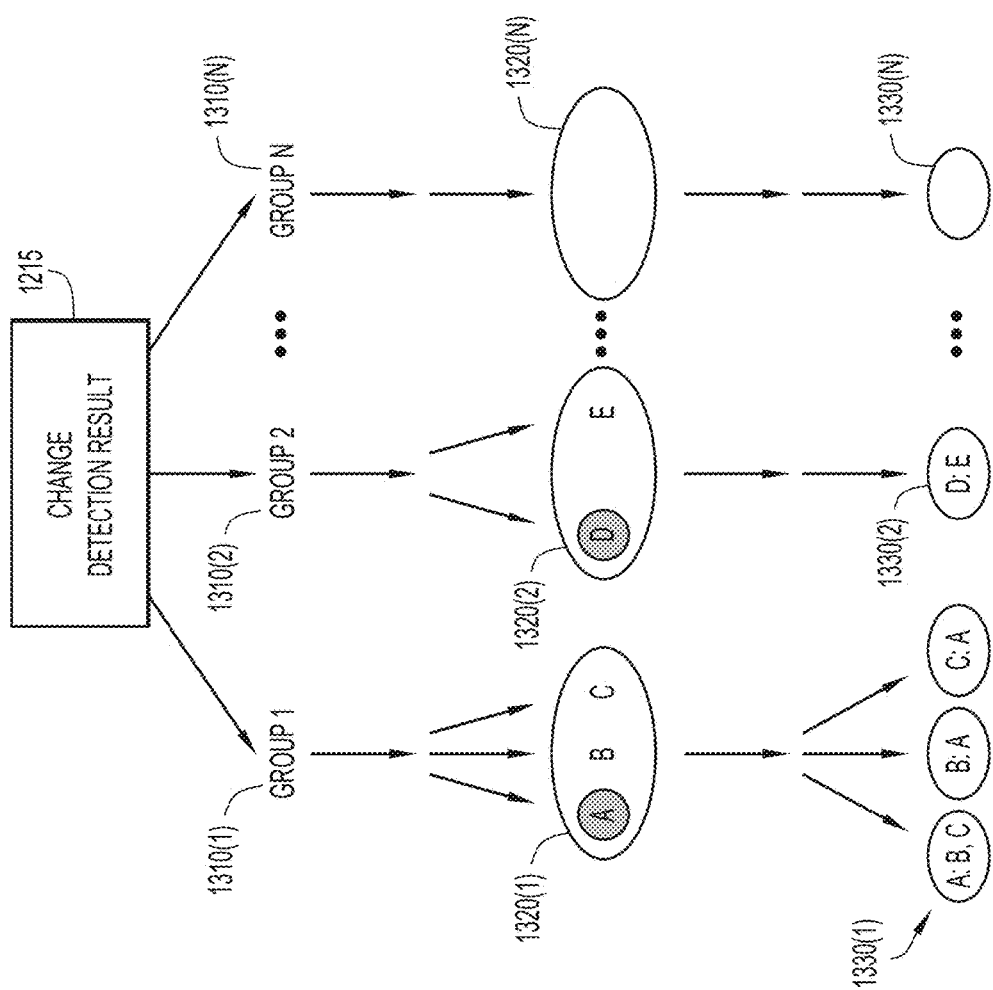
FIG. 13 is a flowchart showing groupings performed by a MOD identification module, according to embodiments of the present disclosure.

FIG. 13 is a flowchart showing groupings performed by MOD identification module 1210. Present techniques leverage domain-knowledge-based schemes to combine drivers with complementary change patterns into offsetting groups and may employ proportional allocation and the maximum migration principle to quantify the impact of each offsetting group.

MOD identification module 1210 monitors utilization offsets of comparable drivers within the same time window. Offsets are identified when utilization patterns of comparable drivers move in opposite directions, Change detection results 1215 are provided as input to MOD identification module. The results may be organized based on groups 1310(1)-1310(N) (e.g., Group 1, Group 2, etc.) using information provided by a knowledge base. Groups may include (e.g., therapeutic classes, procedures, type of services, etc.).

Within each group, indicators may be further analyzed to determine a moving direction. For example, group 1 may comprise components A, B, and C (immunosuppressants), and group 2 may comprise components D and E (small molecules). Component A may be increasing in utilization, while components B and C may be decreasing in utilization. For group 2, component D may be increasing in utilization while component E is decreasing in utilization. Respective groups are shown as groups 1320(1), 1320(2), and 1320(N) MOD identification module 1210 may output each combination moving in opposite directions. Thus, the moving direction of the utilization patterns of all comparable drivers may be labeled. In this example A and B, C are moving in different directions, while D and B are moving in different directions. These combinations may be enumerated as shown in groups 1330(1) to 1330(N).

Offset tracking may be performed at different levels of healthcare data hierarchy. Sample offsets include drugs, place of services, disease severity, communications channel, etc. For drugs, potential substitutions of drugs within same therapeutic classes (Redbook) and per published evidence (Micromedex) for treating the same medical conditions may be analyzed. For place of services, behavioral shifts in care settings may be identified (e.g., potential migration between places of service for treating the same medical conditions). For disease severity, health shifts may be identified (e.g., potential migration between different disease stages of the same disease). For communications channels, patient reported preferences on modes of communications may be analyzed (e.g., email, live phone call, automated phone call, mobile app, etc.).

In general, methods for identifying offsetting treatment options and quantifying corresponding cost impacts may comprise the following components: for each medical condition, comparable treatment options are identified based on the hierarchy (see, e.g., FIG. 17), and MOD groups, i.e., the comparable treatment options whose utilizations (e.g., episode to enrollee ratios) are detected to change in opposite directions, are identified. The amount of utilization change is calculated for each treatment option in the MOD groups.

For each medical condition, the volumes of inflow and outflow offset are determined for all comparable treatment options in the MOD groups according to the proportional allocation assumptions and the maximum migration principle. Proportional allocation assumptions include: (1) assuming that the volume of outflow offset from a treatment option that experiences utilization decrease (the originator) to a comparable treatment option that experiences utilization increase (the receiver) is proportional to the amount of observed utilization increase of the receiver; and (2) assuming that the total volume of outflow offset from an originator is proportional to the amount of observed utilization decrease of the originator. The maximum migration principle assumes that (1) the outflow offset volumes from originators to receivers are determined by maximizing the total amount of outflow offset from all originators under the constraints of proportional allocation, and that (2) the inflow offset volume of each receiver is determined by summing the outflow volumes from all originators.

For each medical condition, the cost impact is computed due to the offset for each treatment option in the MOD groups by using offset adjusted utilization (e.g., episode to enrollee ratio adjusted by inflow or outflow offset) under the assumption of no change in average cost per episode.

Figure 14:
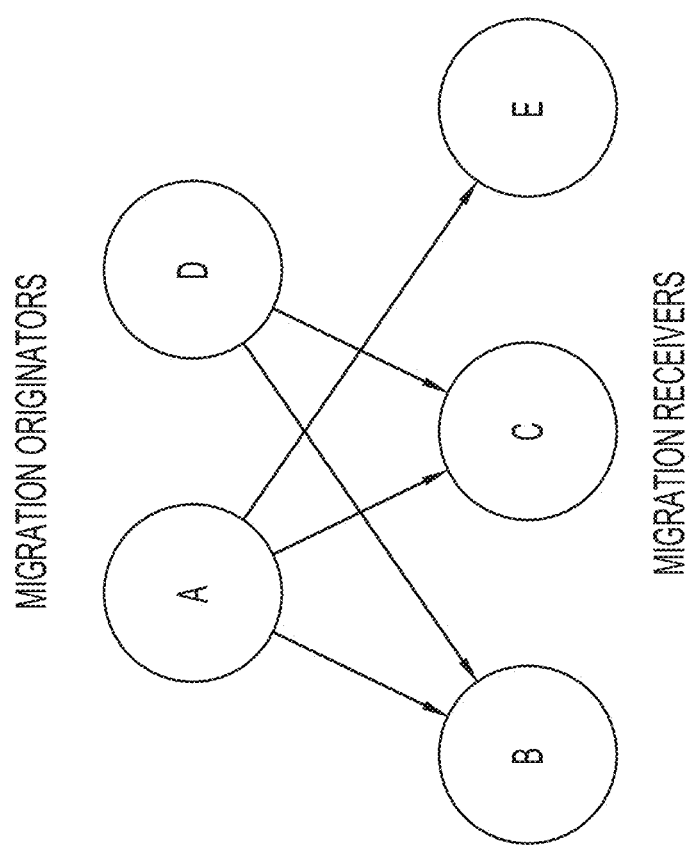
FIG. 14 is an illustration showing migration originators and receivers for a MOD impact evaluation module, according to embodiments of the present disclosure.

FIG. 14 is an illustration showing migration originators and receivers for MOD impact evaluation module 1220. Impact may be estimated using sub-population level data, without using individual-level data. Sub-population analysis not only improves computational speed and reduces analytic complexity, but also protects individual identity in a non-PHI environment, Without tracking each subject (in this case, each patient), the aggregated subjects coming into and out of each originator and receiver are observed. Thus, explicit tracking of specific patients that lead to observed changes are not performed. Instead, changes due to migration, new comers, or drop-outs are estimated without direct observation of specific patients.

Networks may be set up based on the following information and assumptions. Migration networks may include originators (utilization decreasing), identified by the following equation:

$$\text{total outflow}=\text{utilization migration out}+\text{drop out}$$

Migration networks may include receivers (utilization up), identified by the following equation:

$$\text{total inflow}=\text{utilization migration in}+\text{newcomer}$$

Within-network utilization migration may be determined based on:

$$\text{utilization migration out}=\text{utilization migration in}$$

and subject to the following migration constraints:

$$\text{utilization migration in}<=\text{total inflow}$$

$$\text{utilization migration out}<=\text{total outflow}$$

In an embodiment, the following assumptions are made, including: 1) the preference of destination by originators is proportional to inflow of qualified receivers; 2) the population of migration from originators is proportional to outflow of originators; and 3) the maximum migration principle holds in that total migration of utilization should be maximized.

For each collection of identified MOD groups, originators and receivers of the migration network may be defined, and the total migration within the identified network may be determined. For example, for each network, the amount of migration contributed by each originator may be determined based on the sum of receiving amounts for each receiver.

Figure 15:
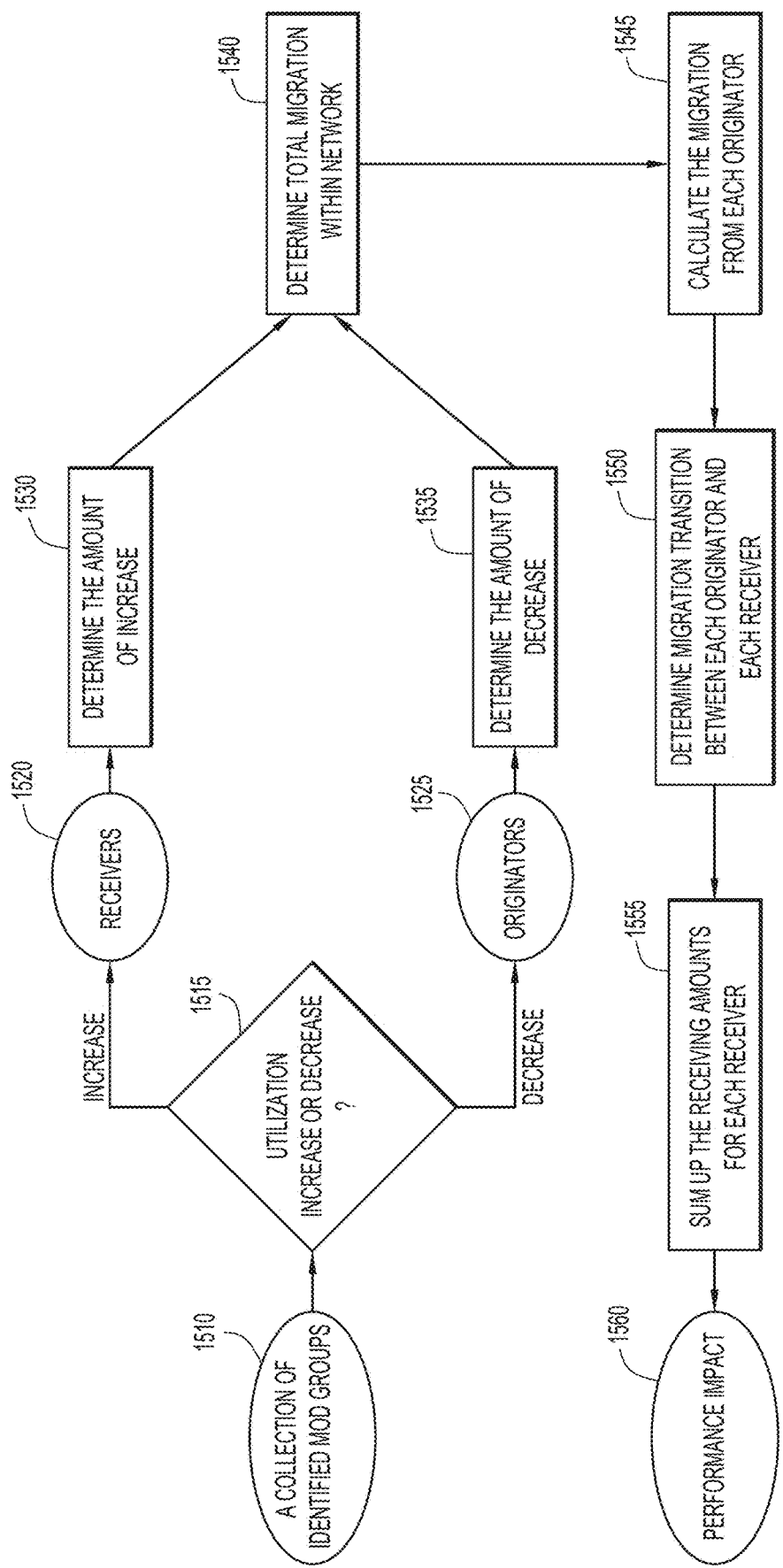
FIG. 15 is a flowchart of operations for implementing a MOD impact evaluation module, according to embodiments of the present disclosure.

FIG. 15 is a flowchart of operations for implementing MOD impact evaluation module 1220. At operation 1510, a collection of identified. MOD groups are received. At operation 1515, the groups are analyzed to determine whether the utilization has increased or decreased. At operation 1520, groups that are identified as increasing are categorized as receivers, and at operation 1530, the amount of increase for each receiver is determined. Similarly, at operation 1525, the groups that are identified as decreasing are categorized as originators, and at operation 1535, the amount of decrease for each originator is determined. Based on this amount, the total migration within the network is determined at operation 1540. At operation 1545, the migration from each originator is determined. At operation 1550, the migration transition between each originator and each receiver is determined. At operation 1555, the receiving amounts are summed up for each receiver. At operation 1560, the performance impact is determined. Thus, by determining migration of amounts or quantities of subjects with respect to migrators or originators, privacy of individual subjects are preserved. Factors of identified performance drivers with opposing utilization trends (e.g., with respect to increasing and decreasing trends) may be identified, and an impact of the identified factors on the performance drivers may be identified based on migration of quantities of subjects (see, e.g., FIG. 14).

Figure 16:
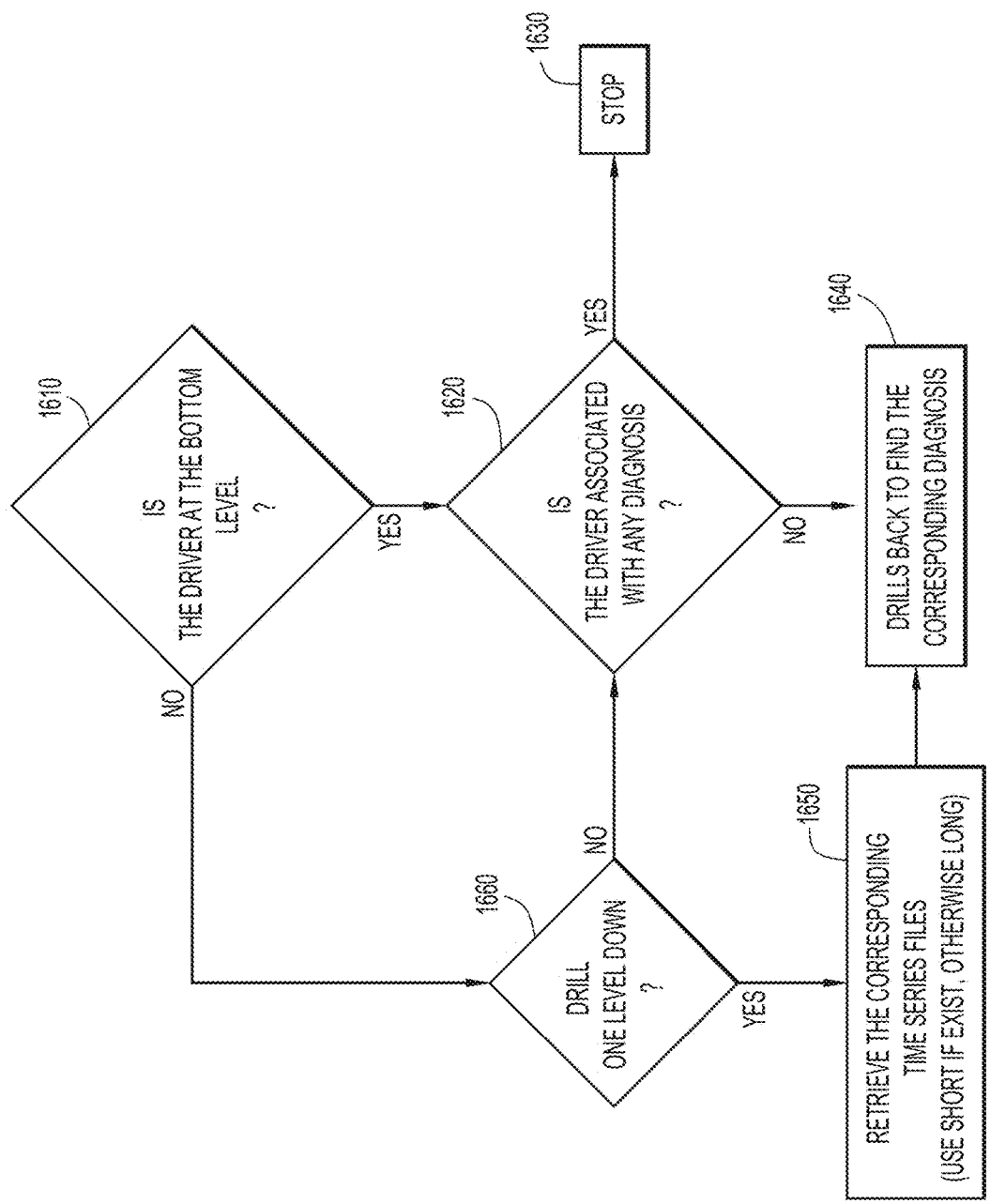
FIG. 16 is a flow chart of example operations for a top drivers and contributors module, according to embodiments of the present disclosure.

FIG. 16 is a flow chart of example operations for top drivers and contributors module 1230. At operation 1610, the system determines whether the driver is at the bottom level. When the driver is at the bottom level, the system proceeds to operation 1620, to determine whether the driver is associated with any diagnosis. If the driver is associated with a diagnosis, the process stops at 1630. If the driver is not associated with a diagnosis, the process proceeds to operation 1640, wherein the system drills back (goes up one or more levels) to find the corresponding diagnosis. At operation 1650, the system retrieves the corresponding time series file.

When the driver is not at the bottom level, the system proceeds to operation 1660, wherein the system traverses one level down. If the system cannot traverse one level down, the system proceeds to operation 1620. Otherwise, the system retrieves the corresponding time series file at operation 1650.

Thus, to identify top drivers and their contributors, all drivers may be ranked by their performance metrics (e.g., cost impact, quality score) and the top drivers identified.

For each driver, hierarchical navigation is permitted, with the user having the ability to drill up to understand the relationship between the parent and the detected change, which is the child node, in order to provide context (e.g., colonoscopy overall (parent node) versus colonoscopy in NY (child node)). The system also allows a user to drill down to identify meaningful contributors. Detected drivers may be grouped based on the viewpoint hierarchy location (e.g., all detected drivers within the same event may be grouped).

In some cases, meta-learning engine 77 may utilize adaptive feedback to incorporate both data-driven and user feedback to improve usefulness and interpretability of results. For example, data-driven feedback may monitor the updated data, conduct re-analysis with more complete data to re-access change type (e.g., using a result tracking method), This approach may help compensate for data censoring, which may lead to misdetection or misclassification of change type. Data driven feedback may estimate a data censoring bias in impact estimation, which can be specific to drivers, and may be used to correct impact calculations that are based on censored data (e.g., proportional adjustments). A modify change detection engine may account for learned bias in alerting change and classifying change, e.g., by a change threshold. These techniques apply updated data to obtain performance drivers with changes satisfying the threshold and to determine the impact of the changes and the impact of factors contributing to the changes for the obtained performance drivers, wherein the updated data includes a more complete set of healthcare related data. By determining a bias in the determination of impact based on the updated data and modifying the impact determination of the changes and factors based on the bias, the threshold for the changes based on the bias may be adjusted. In some aspects, updated data may be applied to obtain performance drivers with changes satisfying the threshold. The impact of the changes and the impact of factors contributing to the changes may be determined for the obtained performance drivers, wherein the updated data includes a more complete set of healthcare related data. A bias in the determination of impact may be determined based on the updated data, and the impact determination of the changes and factors may be modified based on the bias. The threshold may be adjusted for the changes based on the bias.

User feedback may be provided to capture usefulness of performance drivers and potential actions to take to improve the system. Feedback can be captured using any suitable technique, including binary (actionable or not), scale (1 to 5), pair-wise comparison (A is more actionable than B), etc. Feedback may be collected into an actionability database, which maps specific drivers to their characteristics (e.g., driver type, viewpoint, change impact amount, etc.). An actionability model may be developed that captures generalized relationships between driver characteristics and actionability (e.g., using any appropriate supervised learning method). Actionability models may be applied in the interpretation engine. For example, in top driver ranking, actionability adjusted cost impact estimates may be used.

For example, feedback from a user pertaining to the ranked performance drivers may be received. A machine learning model may be applied to learn relationships between characteristics of the ranked performance drivers and corresponding actions based on the feedback from the user. The impact of the determined changes and the impact of the identified factors of the identified performance drivers based on the learned relationships may be modified, and the identified performance drivers may be ranked based on the modified impact of the determined changes and the modified impact of the identified factors.

Figure 17:
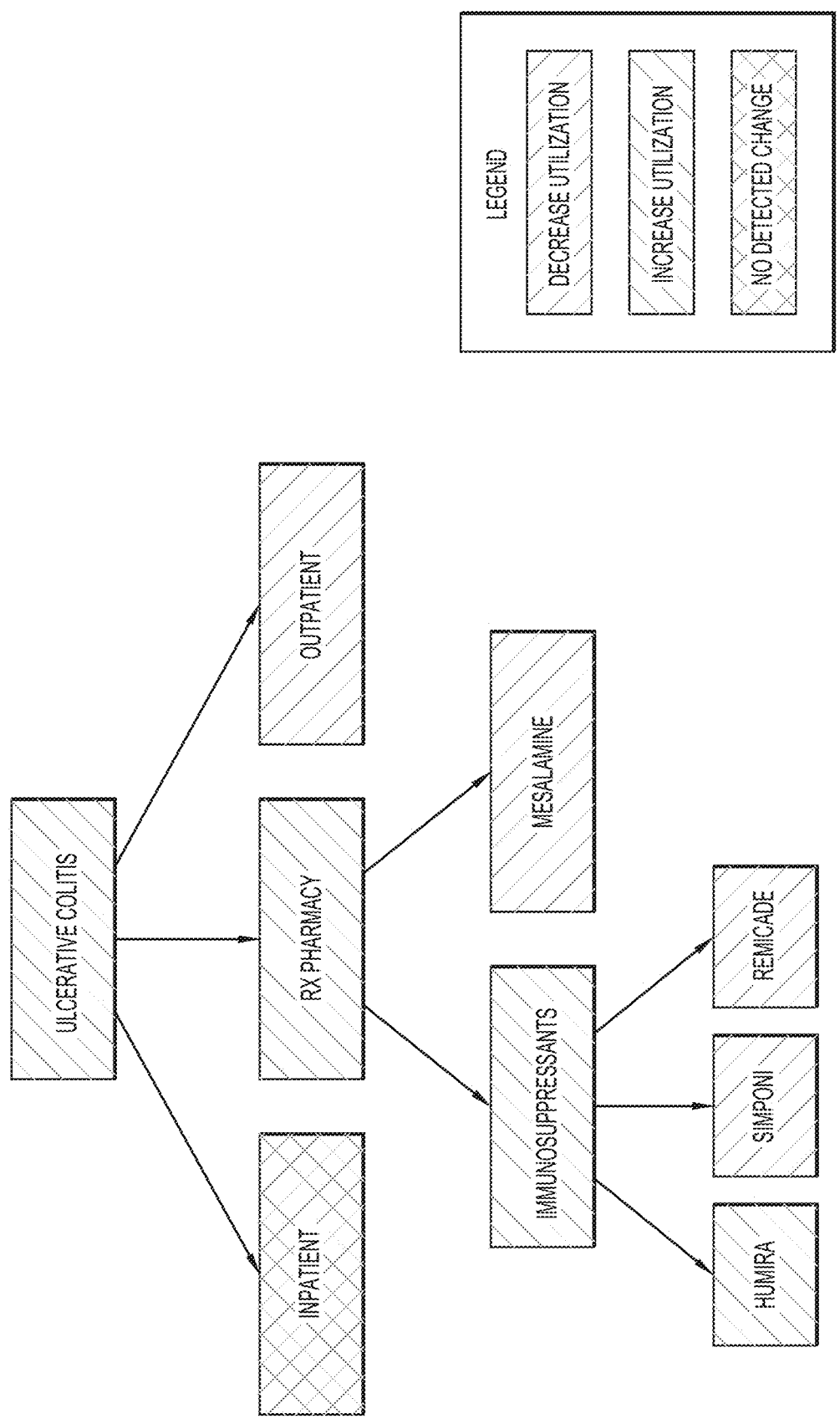
FIG. 17 is a flowchart showing a hierarchical viewpoint of healthcare data for ulcerative colitis, according to embodiments of the present disclosure.

FIG. 17 is a flowchart showing hierarchical viewpoint of healthcare: data, A hierarchical viewpoint may allow detection of change patterns for high-dimensional, large-scale, and noisy healthcare time series data. With this type of representation, a user can identify performance indicator change patterns and attribute such changes to one or more drivers. Once the cost change patterns are identified and interpreted by a user or the system, a user may take action to manage such changes.

Healthcare data is often characterized as having a high dimensionality with fragmented data. For example, healthcare data may have an extremely large number of potential drivers and factors with great disparity of data availability. When analyzing healthcare data, the amount of data may influence results. For example, sparse data may lead to false discoveries or other artifacts due to sampling error. Accordingly, large data sets that are representative samples of a large population are desirable (e.g., such as medical insurance claims data). Other factors which may influence results include natural variability (e.g., seasonality of a disease such as influenza), censoring data (e.g., due to delays in processing claims data), and temporal changes (e.g., sequential dependence of changes in health data, identified using autocorrelation). Cost change drivers in healthcare are often interrelated, making analysis of such healthcare data difficult to delineate and interpret. Change driver detection techniques may be used to address these issues.

The following provides an example of how the present techniques may be used for detecting performance drivers in large-scale healthcare data. FIG. 17 shows a hierarchical representation of healthcare data relating to ulcerative colitis, Cost drivers may be represented by a domain knowledge-based hierarchical structure (see, e.g., FIGS. 4, 5) and data may be aggregated accordingly based on the structure. In this example, ulcerative colitis is at the top (nth level) of the hierarchy, the type of service (e.g., inpatient, outpatient, Rx pharmacy) is at the next level down ((n−1)th level) of the hierarchy. The Rx category contains additional levels, at the (n−2)th level, including small molecules (mesalamine) and immunosuppressants, with the immunosuppressants including Humira, Simponi, and Remicade. The hierarchical viewpoint is represented in a way that illustrates changes in utilization (e.g., decreased utilization, increased utilization, or no detected change), With reference to the (n−1)th level, an increase in utilization is shown for Rx Pharmacy, while a decrease in utilization is shown for Outpatient. No change was detected for Inpatient. Drilling down to the (n−2)th level, an increase in utilization was detected for immunosuppressants, while a decrease in utilization was detected for mesalamine. Drilling down to the next level, the (n−3)th level, an increase in utilization was observed for Humira, while a decrease in utilization was detected for Simponi and Remicade.

This technique may be used to monitor "utilization offsets" of comparable treatment options (e.g., utilization of branded versus generic drugs) for the same medical conditions (e.g., ulcerative colitis, cancer, diabetes, etc.) within the same time window. For example, the immunosuppressant category may include biosimilars, or the small molecule category may include generics. The system may show a decrease in overall cost for treating the condition, once a generic or biosimilar version is available. Present techniques allow the cost impact attributable to the offset effect to be estimated. For example, an insurer may adopt the generic or biosimilar in its respective formulary to control costs.

Figure 18:
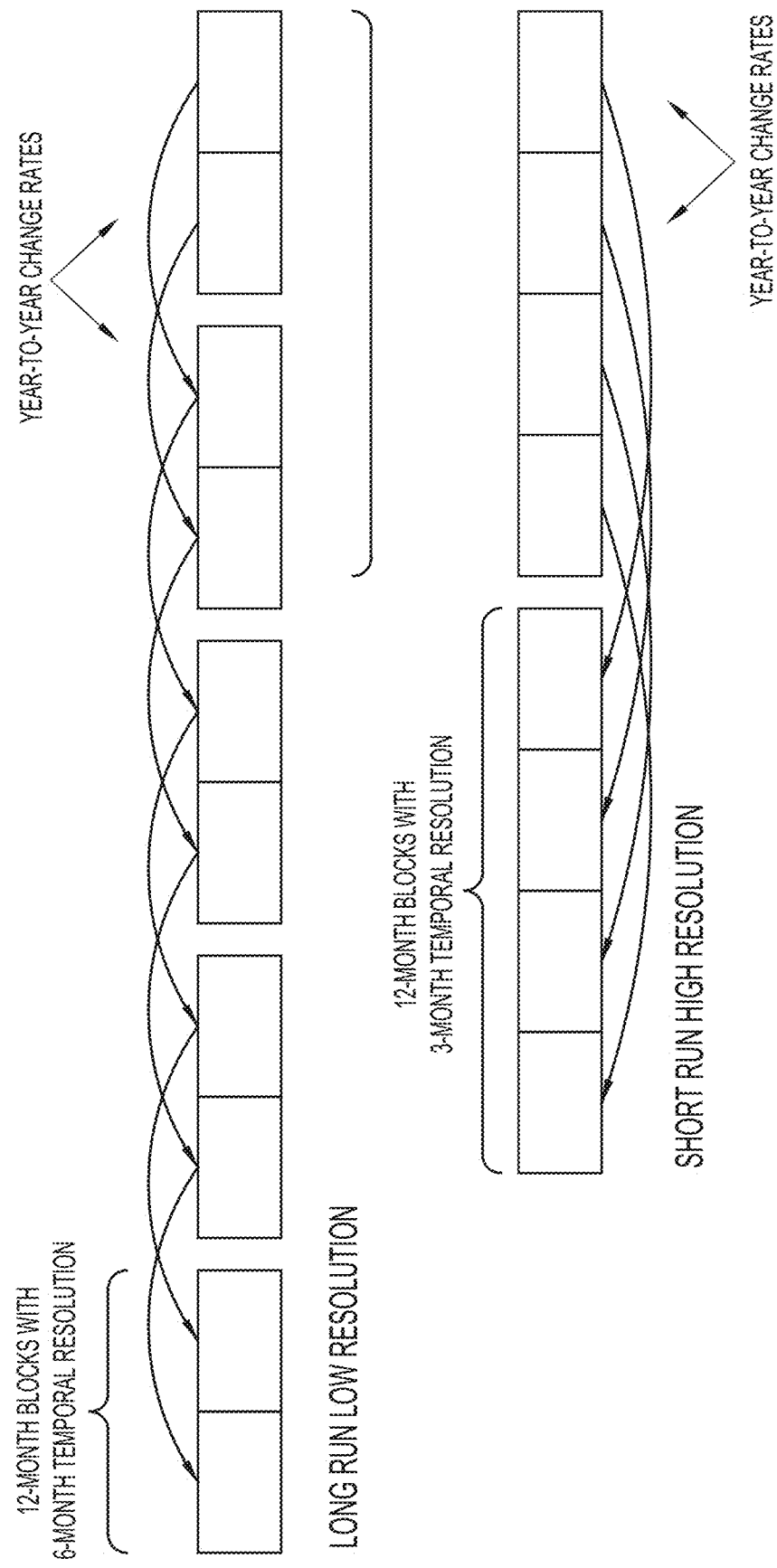
FIG. 18 is an illustration showing detection of changes in a performance driver, according to embodiments of the present disclosure.

FIG. 18 is an illustration showing detection of changes in a performance driver, such as utilization, wherein data may be aggregated temporally using multiple time windows with different durations and resolutions. Multi-resolution change pattern detection and characterization employs multi-resolution temporal aggregation schemes (e.g., long-run low-resolution and short-run high-resolution) to detect and characterize change patterns. Sets of performance indicators may be analyzed based on the time windows and mapped attributes. For example, a long nm low resolution analysis is shown in which each block represents 12 months, with each block subdivided into two six month blocks. A section of the long run low resolution block may be selected and analyzed with higher granularity. For example, each year may be analyzed with a short run high resolution block, for example, with 3-month temporal resolution blocks. Year to year changes may be analyzed, e.g., the first quarter of each year may be analyzed as a function of time to detect various changes.

Figure 19:
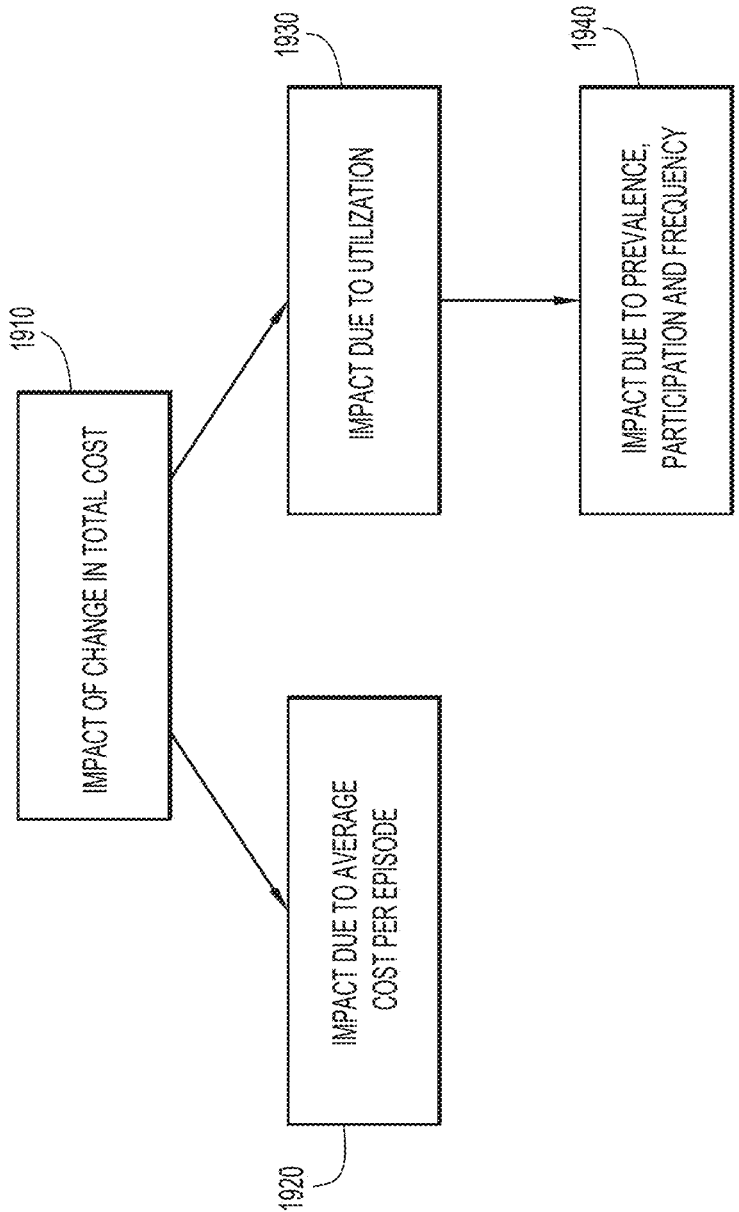
FIG. 19 is a flow chart showing interrelated components of multi-KPI change attribution, according to embodiments of the present disclosure.

FIG. 19 is a flow chart showing interrelated components of multi-KPI change attribution. When multiple interrelated factors are present, determining the impact of each factor may be difficult. In this example, the total cost is provided by the following formula:

total cost=(average cost per episode)*(episode to enrollee ratio)*(# enrollees), wherein the episode to enrollee ratio=(patient to enrollee ratio)*(claimant to patient ratio)*(episode to claimant ratio).

Here, the total change is decomposed into multiple performance indicators, wherein utilization=episode to enrollee ratio; prevalence=patient to enrollee ratio; participation=claimant to patient ratio; frequency=episode to claimant ratio. The impact may be analyzed for each performance indicator. Component 1910 shows impact of Change in total cost. Component 1910 may be represented as two components, component 1920 corresponding to an impact due to average cost per episode and component 1930 corresponding to an impact due to utilization. Utilization may be represented by additional components 1940, which include prevalence, participation and frequency. Additionally, these changes may be detected based on year-to-year comparison of the KPIs. Thus, impact of seasonality can be mitigated, By excluding claims with delays in processing time that exceed certain thresholds, KPIs may be determined in a manner that mitigates false effects from censorship.

Figure 20:
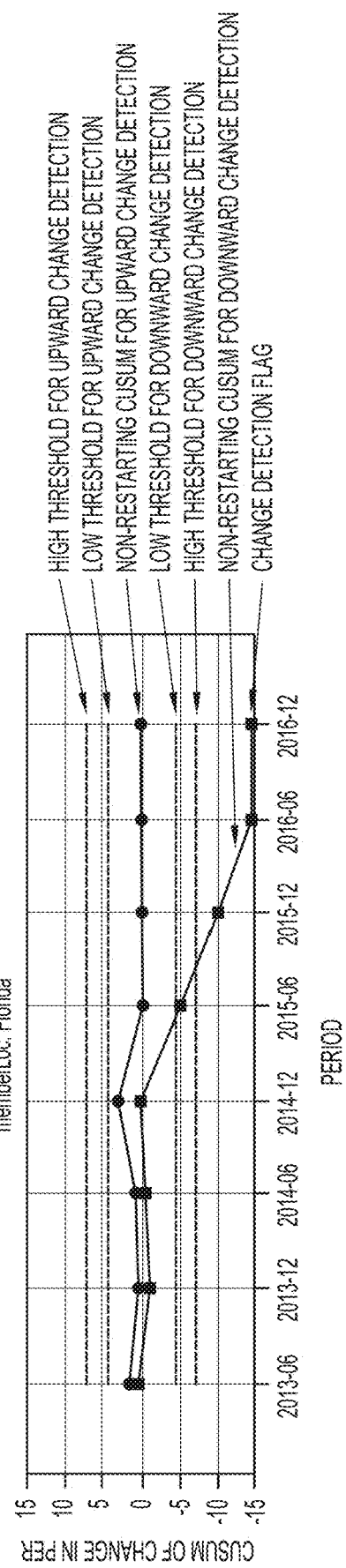
FIG. 20 shows examples of using modified SPC algorithms with learned detection thresholds, according to embodiments of the present disclosure.

FIG. 20 shows examples of using modified SPC algorithms with learned detection thresholds. These SPC algorithms automatically account for multiple change points (e.g., non-restarting cumulative sum control chart (CUSUM) and may use one or more detection thresholds to control the false detection rate at the last period). Detection thresholds may be learned via simulation or statistical theory to account for sampling errors and possible serial dependence of change rates. Thus, hierarchical and/or multi-resolution analysis may be used to characterize change patterns (e.g., growth in the cost of a particular treatment option for a given condition with no change in overall cost). In this example, high and low thresholds are shown for upward change detection. High and low thresholds are shown for downward change detection. Non-restarting CUSUMs are also shown for upward change detection and for downward change detection.

FIG. 21 shows examples of change patterns that may be characterized by rules-based techniques according to the results of multi-resolution analysis. In some aspects, change patterns may be characterized by unsupervised clustering according to the signatures of change rates (e.g., step-like growth, linear growth, oscillatory growth). In this example, short-run high resolution analysis and long-run low resolution analysis results are analyzed for various changes, including emerging growth, emerging decline, persistent growth, persistent decline, stabilizing growth, and stabilizing decline. As shown by the figure, short-run and long-run results may reveal different changes.

Figure 22A:
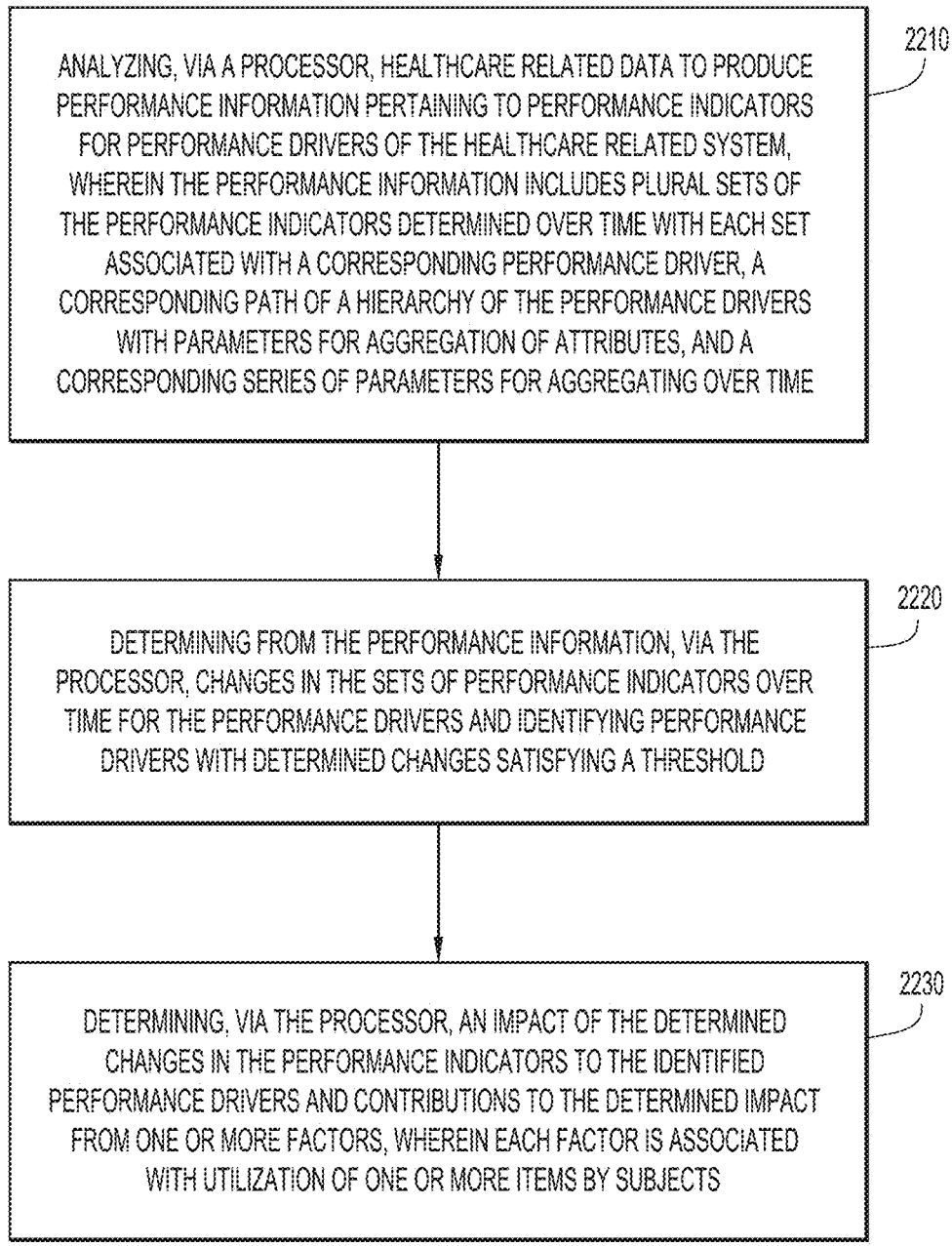
FIG. 22A is a high level operational flow chart of identifying and ranking performance drivers in a hierarchical data structure, according to embodiments of the present disclosure.
Figure 22B:
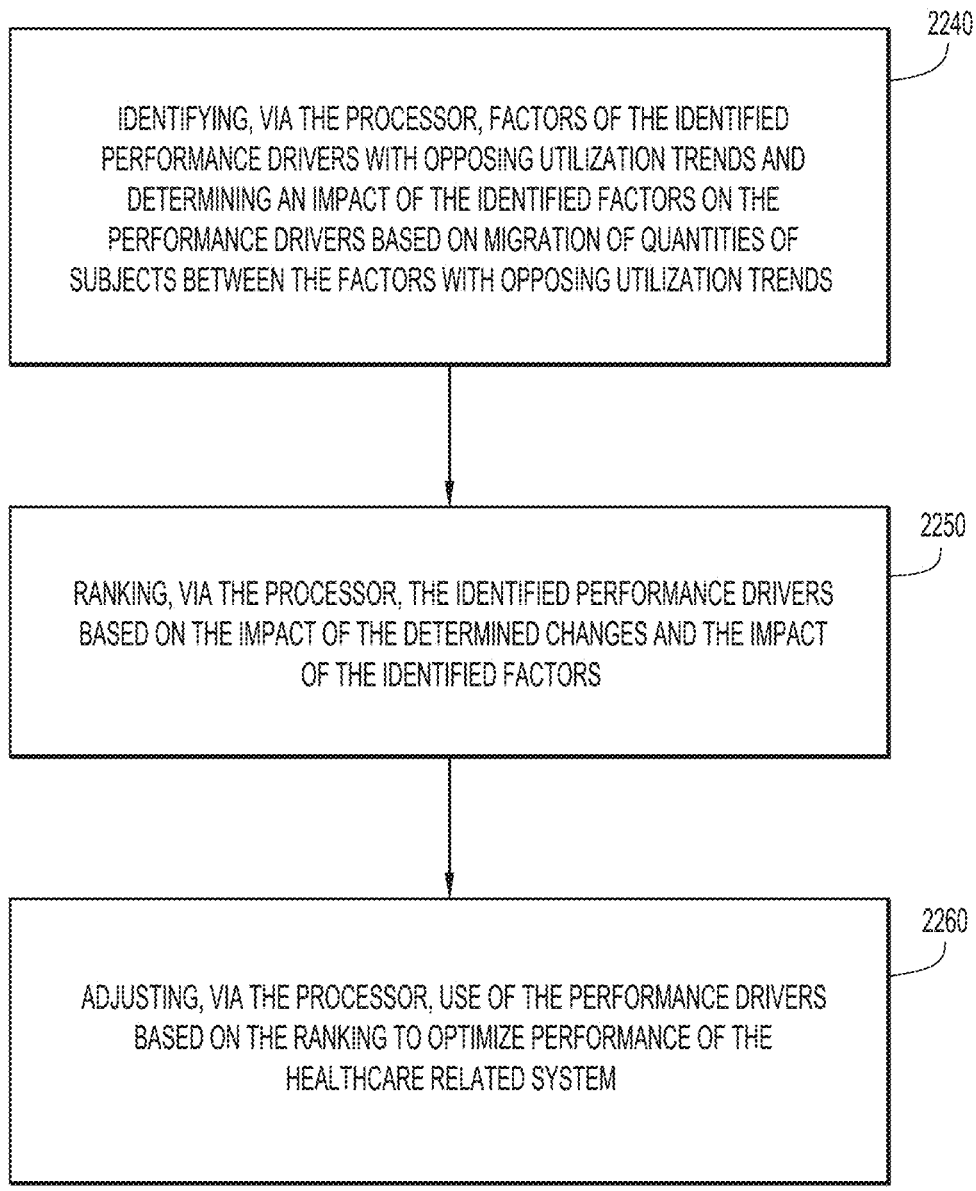
FIG. 22B is continuation of the high level operational flow chart of FIG. 22A, according to embodiments of the present disclosure.

FIGS. 22A-22B shows a high level operational flow chart of identifying and ranking performance drivers in a hierarchical data structure. At operation 2210, healthcare related data is analyzed to produce performance information pertaining to performance indicators for performance drivers of the healthcare related system, wherein the performance information includes plural sets of the performance indicators determined over time with each set associated with a corresponding performance driver, a corresponding path of a hierarchy of the performance drivers with parameters for aggregation of attributes, and a corresponding series of parameters for aggregating over time. At operation 2220, changes in the sets of performance indicators over time for the performance drivers are determined and performance drivers with determined changes satisfying a threshold are identified. At operation 2230, an impact of the determined changes in the performance indicators to the identified performance drivers and contributions to the determined impact from one or more factors are identified, wherein each factor is associated with utilization of one or more items by subjects. At operation 2240, factors of the identified performance drivers with opposing utilization trends are identified, and an impact of the identified factors on the performance drivers based on migration of quantities of subjects between the factors with opposing utilization trends are determined. At operation 2250, the identified performance drivers are ranked based on the impact of the determined changes and the impact of the identified factors. At operation 2260, use of the performance drivers are adjusted based on the ranking to optimize performance of the healthcare related system.

Present techniques provide the ability to search, detect and disentangle changes in a complex outcome metric wherein the overall outcome metric is represented as a total performance score of the system (e.g., total healthcare spent, service utilization, overall provider performance, etc.) and the total performance score is decomposable into multiple drivers. Drivers are represented as a hierarchical structure (e.g., different drill paths in a healthcare data hierarchy, see FIG. 4, or as different sub-domains of quality measures, FIG. 5). Each driver may have its own performance score. For each analysis hierarchy, the sum of individual drivers' performance scores in the child layer should be equal to the performance score of their parent. Each performance score can be further attributed to multiple performance dimensions, for example, the system may break the performance score into KPIs, and the KPIs can be additive or multiplicative (e.g., spend is a multiple of utilization and unit spend, a length-of-stay score is a multiple of a number of overstayed admissions and the average length of overstayed, etc.) The system is designed to surface high impact, actionable and interpretable drivers.

Other advantages of present techniques include mining data with missing information, in particular, for sparse datasets in which individual patient data is not available due to privacy concerns. Thus, the database is limited to information on total usage of the treatment at the population level, protecting individual patient privacy. The present techniques may use a principle of maximum migration (and variants) to resolve the ambiguity due to missing information and devise a method to arrive at a reasonable (typically unique) solution.

Present techniques use a detection process that is fast, comprehensive, and objective. These techniques support early detection of change drivers, with flexibility to tune detection sensitivity. Additionally, a contextual-based approach to improve actionability is used, and detected drivers are specific, high impact, and interpretable. The output of the system is easily customizable to end user's specific needs and feedback.

In some examples, the system may select the highest ranked driver, and may update the healthcare system based on this driver. For example, if the cost of a therapeutic increases, the system may determine whether a generic or biosimilar equivalent is available, and may add the lower cost alternative to the formulary of the insurance company.

In general, present techniques may be used to reduce healthcare costs by refining or limiting services and therapeutics that are at a high cost relative to their counterparts (e.g., a physician, hospital, pharmacy, etc. who charges a substantially higher rate than his/her/their counterparts may be contacted for renegotiation of rates, costs, tees, etc.). In some aspects, notifications may be sent to healthcare administrators of the insurance companies, regarding driver changes (e.g., increases or decreases) within a particular time period, to promote rapid identification and review of these changes.

Present techniques detect performance drivers such as cost change drivers in large-scale healthcare data using: (1) a hierarchical and/or multi-resolution search strategy, wherein drivers are represented by a domain knowledge-based hierarchical structure and data are aggregated temporally using multiple analysis windows with different duration and resolution; (2) Multi-KPI change attribution techniques, in which the total change is decomposed into multiple explanatory factors; (3) de-seasonalized and self-censored rates of change, in which changes are detected based on year-to-year comparison of the KPIs, wherein the KPIs are calculated by excluding claims with delays in processing time that exceed certain thresholds; (4) modified SPC algorithms with learned detection thresholds that employ SPC algorithms that automatically account for multiple change points (e.g., non-restarting CUSUM) and use one or more detection thresholds to control the false detection rate at the last period, wherein detection thresholds are learned via simulation or statistical theory to account for sampling errors and possible serial dependence of change rates; and (5) hierarchical and/or multi-resolution characterization schemes that allow change patterns to be identified according to the hierarchy (e.g., growth in the cost of a particular treatment option for a given condition but no change in its overall cost), wherein change patterns are characterized by rules-based techniques according to the results of multi-resolution analysis, and wherein change patterns are characterized by unsupervised clustering according to the signatures of change rates (e.g., step-like growth, linear growth, oscillatory growth).

It will be appreciated that the embodiments described above and illustrated in the drawings represent only a few of the many ways of implementing embodiments for identifying performance drivers. These embodiments are suitable for multi-dimensional analysis, and in particular, for analyzing combinations of attributes and drivers over time. These techniques may be implemented in an automated manner to detect changes (e.g., changes in performance indicators and drivers).

The environment of the present invention embodiments may include any number of computer or other processing systems (e.g., client or end-user systems, server systems, etc.) and databases or other repositories arranged in any desired fashion, where the present invention embodiments may be applied to any desired type of computing environment (e.g., cloud computing, client-server, network computing, mainframe, stand-alone systems, etc.). The computer or other processing systems employed by the present invention embodiments may be implemented by any number of any personal or other type of computer or processing system (e.g., desktop, laptop, PDA, mobile devices, etc.), and may include any commercially available operating system and any combination of commercially available and custom software (e.g., browser software, communications software, server software, healthcare data system 15, including PHI environment 70 and non-PHI environment 74, etc.). These systems may include any types of monitors and input devices (e.g., keyboard, mouse, voice recognition, etc.) to enter and/or view information.

It is to be understood that the software (e.g., healthcare data system 15, including PHI environment 70 and non-PHI environment 74, etc.) of the present invention embodiments may be implemented in any desired computer language and could be developed by one of ordinary skill in the computer arts based on the functional descriptions contained in the specification and flow charts illustrated in the drawings. Further, any references herein of software performing various functions generally refer to computer systems or processors performing those functions under software control. The computer systems of the present invention embodiments may alternatively be implemented by any type of hardware and/or other processing circuitry.

The various functions of the computer or other processing systems may be distributed in any manner among any number of software and/or hardware modules or units, processing or computer systems and/or circuitry, where the computer or processing systems may be disposed locally or remotely of each other and communicate via any suitable communications medium (e.g., LAN, WAN, Intranet, Internet, hardwire, modem connection, wireless, etc.). For example, the functions of the present invention embodiments may be distributed in any manner among the various end-user/client and server systems, and/or any other intermediary processing devices. The software and/or algorithms described above and illustrated in the flow charts may be modified in any manner that accomplishes the functions described herein. In addition, the functions in the flow charts or description may be performed in any order that accomplishes a desired operation.

The software of the present invention embodiments (e.g., healthcare data system 15, including PHI environment 70 and non-PHI environment 74, etc.) may be available on a non-transitory computer useable medium (e.g., magnetic or optical mediums, magneto-optic mediums, floppy diskettes, CD-ROM, DVD, memory devices, etc.) of a stationary or portable program product apparatus or device for use with stand-alone systems or systems connected by a network or other communications medium.

The communication network may be implemented by any number of any type of communications network (e.g., LAN, WAN, Internet, Intranet, VPN, etc.). The computer or other processing systems of the present invention embodiments may include any conventional or other communications devices to communicate over the network via any conventional or other protocols. The computer or other processing systems may utilize any type of connection (e.g., wired, wireless, etc.) for access to the network. Local communication media may be implemented by any suitable communication media (e.g., local area network (LAN), hardwire, wireless link, Intranet, etc.).

The system may employ any number of any conventional or other databases, data stores or storage structures (e.g., files, databases, data structures, data or other repositories, etc.) to store information (e.g., healthcare data 42, analytic results 44, user feedback 46, and other information associated with viewpoint hierarchies and analyzing performance indicators and performance drivers, etc.). The database system may be implemented by any number of any conventional or other databases, data stores or storage structures (e.g., files, databases, data structures, data or other repositories, etc.) to store information (e.g., healthcare data 42, analytic results 44, user feedback 46, and other information associated with viewpoint hierarchies and analyzing performance indicators and performance drivers, etc.). The database system may be included within or coupled to the server and/or client systems. The database systems and/or storage structures may be remote from or local to the computer or other processing systems, and may store any desired data (e.g., healthcare data 42, analytic results 44, user feedback 46, and other information associated with viewpoint hierarchies and analyzing performance indicators and performance drivers, etc.).

The present invention embodiments may employ any number of any type of user interface (e.g., Graphical User Interface (GUI), command-line, prompt, etc.) for obtaining or providing information (e.g., healthcare data 42, analytic results 44, user feedback 46, and other information associated with viewpoint hierarchies and analyzing performance indicators and performance drivers, etc.), where the interface may include any information arranged in any fashion. The interface may include any number of any types of input or actuation mechanisms (e.g., buttons, icons, fields, boxes, links, etc.) disposed at any locations to enter/display information and initiate desired actions via any suitable input devices (e.g., mouse, keyboard, etc.). The interface screens may include any suitable actuators (e.g., links, tabs, etc.) to navigate between the screens in any fashion.

The report may include any information arranged in any fashion, and may be configurable based on rules or other criteria to provide desired information to a user (e.g., information about performance indicators and performance drivers, including cost drivers, utilization drivers, etc.).

The present invention embodiments are not limited to the specific tasks or algorithms described above, but may be utilized for any suitable healthcare setting in which spend/cost analysis (from claims, billing) may be used to drive changes in dollars spent on healthcare. Present techniques are also useful for utilization analysis (from EMR, claims) and may guide an understanding of factors driving changes in utilization of healthcare services. Techniques may be used for performing quality metrics analyses (from claims, billing, EMR, patient-reported outcome) to understand factors driving changes in quality metrics.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises", "comprising", "includes", "including", "has", "have", "having", "with" and the like, when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams anchor flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A method of identifying and optimizing performance drivers of a healthcare related system comprising:
retrieving from a first database, via a processor, healthcare related data pertaining to a query for performance driver information of the healthcare related system;
analyzing, via the processor, the healthcare related data to produce performance information pertaining to performance indicators for performance drivers that affect performance of the healthcare related system, wherein the performance information includes plural sets of the performance indicators determined over time with each set associated with a corresponding performance driver, and wherein the performance indicators are aggregated according to arrangement of the performance drivers in a hierarchy;
determining from the performance information, via the processor, changes in the sets of performance indicators over time for the performance drivers and identifying performance drivers with determined changes satisfying a threshold;
determining, via the processor, an impact of the determined changes in the performance indicators to the identified performance drivers and contributions to the determined impact from one or more factors, wherein each of the factors is associated with utilization of one or more items by subjects;
identifying, via the processor, the factors contributing to the determined impact to the identified performance drivers with opposing utilization trends and determining an impact of the identified factors on the identified performance drivers by:
monitoring utilization of the items of the factors of comparable performance drivers and identifying groups of the factors of the comparable performance drivers with opposing utilization trends for the items, wherein the arrangement of the performance drivers in the hierarchy indicates the comparable performance drivers;
determining quantities of subjects migrating between the factors with a decreasing utilization trend and the factors with an increasing utilization trend within each of the identified groups, wherein the migration of subjects is determined from population-based data to preserve privacy of individual subjects; and
determining the impact of the identified factors on the identified performance drivers based on migration of the quantities of subjects between the factors with opposing utilization trends;
ranking, via the processor, the identified performance drivers based on the impact of the determined changes and the impact of the identified factors to produce results for the query;
receiving, via the processor, updated data and feedback from a user over time;
adjusting the threshold based on the updated data, via the processor, and continually detecting changes in the sets of performance indicators over time for the performance drivers to alter the identified performance drivers based on the adjusted threshold and modify the ranking of the identified performance drivers;
storing the feedback in a second database mapping the performance drivers of the modified ranking to corresponding characteristics;
training, via the processor, a supervised machine learning model over time with mappings from the second database to learn relationships between the characteristics of the performance drivers of the modified ranking and corresponding actions as the updated data and feedback from the user are received over time;
determining, via the supervised machine learning model of the processor, relationships between the performance drivers of the modified ranking and the corresponding actions;
modifying, via the processor, the impact of the determined changes and the impact of the identified factors of the identified performance drivers based on the relationships determined by the supervised machine learning model;
altering, via the processor, the modified ranking of the identified performance drivers based on the modified impact of the determined changes and the modified impact of the identified factors; and
adjusting, via the processor, performance of actions based on the corresponding actions of the ranked performance drivers in the altered ranking to optimize performance of the healthcare related system.

2. The method of claim 1, wherein analyzing the healthcare related data comprises:
organizing the healthcare related data based on time windows;
assigning an event label to data records and grouping the data records into events based on the assigned event label;
mapping attributes of the data records according to hierarchical medical concepts; and
determining the sets of performance indicators based on the time windows and mapped attributes.

3. The method of claim 1, further comprising:
applying a machine learning model to adjust the threshold for the determined changes for identifying the performance drivers.

4. The method of claim 1, further comprising:
classifying the determined changes into change patterns, wherein the change patterns include multiresolution change detection results and each indicate a direction and a rate of change.

5. The method of claim 4, wherein the classifying is performed by a machine learning classifier.

6. The method of claim 4, wherein the classifying is performed by a rules-based classifier.

7. The method of claim 1, further comprising:
determining relationships between the ranked performance drivers based on navigation within the hierarchy of performance drivers.

8. The method of claim 1, further comprising:
applying the updated data to obtain performance drivers with changes satisfying the threshold and to determine the impact of the changes and the impact of factors contributing to the changes for the obtained performance drivers, wherein the updated data includes a more complete set of healthcare related data;
determining a bias in the determination of impact based on the updated data and modifying the impact determination of the changes and factors based on the bias; and
adjusting the threshold for the changes based on the bias.

9. A computer system for identifying and optimizing performance drivers of a healthcare related system, wherein the computer system comprises at least one processor configured to:
retrieve from a first database healthcare related data pertaining to a query for performance driver information of the healthcare related system;
analyze the healthcare related data to produce performance information pertaining to performance indicators for performance drivers that affect performance of the healthcare related system, wherein the performance information includes plural sets of the performance indicators determined over time with each set associated with a corresponding performance driver, and wherein the performance indicators are aggregated according to arrangement of the performance drivers in a hierarchy;
determine from the performance information changes in the sets of performance indicators over time for the performance drivers and identify performance drivers with determined changes satisfying a threshold;

determine an impact of the determined changes in the performance indicators to the identified performance drivers and contributions to the determined impact from one or more factors, wherein each of the factors is associated with utilization of one or more items by subjects;

identify the factors contributing to the determined impact to the identified performance drivers with opposing utilization trends and determine an impact of the identified factors on the identified performance drivers by:

monitoring utilization of the items of the factors of comparable performance drivers and identifying groups of the factors of the comparable performance drivers with opposing utilization trends for the items, wherein the arrangement of the performance drivers in the hierarchy indicates the comparable performance drivers;

determining quantities of subjects migrating between the factors with a decreasing utilization trend and the factors with an increasing utilization trend within each of the identified groups, wherein the migration of subjects is determined from population-based data to preserve privacy of individual subjects; and determining the impact of the identified factors on the identified performance drivers based on migration of the quantities of subjects between the factors with opposing utilization trends;

rank the identified performance drivers based on the impact of the determined changes and the impact of the identified factors to produce results for the query;

receive updated data and feedback from a user over time;

adjust the threshold based on the updated data and continually detect changes in the sets of performance indicators over time for the performance drivers to alter the identified performance drivers based on the adjusted threshold and modify the ranking of the identified performance drivers store the feedback in a second database mapping the performance drivers of the modified ranking to corresponding characteristics;

train a supervised machine learning model over time with mappings from the second database to learn relationships between the characteristics of the performance drivers of the modified ranking and corresponding actions as the updated data and feedback from the user are received over time;

determine, via the supervised machine learning model, relationships between the performance drivers of the modified ranking and the corresponding actions;

modify the impact of the determined changes and the impact of the identified factors of the identified performance drivers based on the relationships determined by the supervised machine learning model;

alter the modified ranking of the identified performance drivers based on the modified impact of the determined changes and the modified impact of the identified factors; and adjust performance of actions based on the corresponding actions of the ranked performance drivers in the altered ranking to optimize performance of the healthcare related system.

10. The computer system of claim 9, wherein the at least one processor is further configured to:

organize the healthcare related data based on time windows;

assign an event label to data records and group the data records into events based on the assigned event label;

map attributes of the data records according to hierarchical medical concepts; and determine the sets of performance indicators based on the time windows and mapped attributes.

11. The computer system of claim 9, wherein the at least one processor is further configured to:

apply a machine learning model to adjust the threshold for the determined changes for identifying the performance drivers.

12. The computer system of claim 9, wherein the at least one processor is further configured to:

classify the determined changes into change patterns, wherein the change patterns include multiresolution change detection results and each indicate a direction and a rate of change.

13. The computer system of claim 12, wherein the classifying is performed by a machine learning classifier.

14. The computer system of claim 9, wherein the at least one processor is further configured to:

determine relationships between the ranked performance drivers based on navigation within the hierarchy of performance drivers.

15. The computer system of claim 9, wherein the at least one processor is further configured to:

apply the updated data to obtain performance drivers with changes satisfying the threshold and to determine the impact of the changes and the impact of factors contributing to the changes for the obtained performance drivers, wherein the updated data includes a more complete set of healthcare related data;

determine a bias in the determination of impact based on the updated data and modify the impact determination of the changes and factors based on the bias; and adjust the threshold for the changes based on the bias.

16. A computer program product for identifying and optimizing performance drivers of a healthcare related system, the computer program product comprising one or more computer readable storage media collectively having program instructions embodied therewith, the program instructions executable by a computer to cause the computer to:

retrieve from a first database healthcare related data pertaining to a query for performance driver information of the healthcare related system;

analyze the healthcare related data to produce performance information pertaining to performance indicators for performance drivers that affect performance of the healthcare related system, wherein the performance information includes plural sets of the performance indicators determined over time with each set associated with a corresponding performance driver, and wherein the performance indicators are aggregated according to arrangement of the performance drivers in a hierarchy;

determine from the performance information changes in the sets of performance indicators over time for the performance drivers and identify performance drivers with determined changes satisfying a threshold;

determine an impact of the determined changes in the performance indicators to the identified performance drivers and contributions to the determined impact from one or more factors, wherein each of the factors is associated with utilization of one or more items by subjects;

identify the factors contributing to the determined impact to the identified performance drivers with opposing utilization trends and determine an impact of the identified factors on the identified performance drivers by:

monitoring utilization of the items of the factors of comparable performance drivers and identifying groups of the factors of the comparable performance drivers with opposing utilization trends for the items, wherein the arrangement of the performance drivers in the hierarchy indicates the comparable performance drivers;

determining quantities of subjects migrating between the factors with a decreasing utilization trend and the factors with an increasing utilization trend within each of the identified groups, wherein the migration of subjects is determined from population-based data to preserve privacy of individual subjects; and determining the impact of the identified factors on the identified performance drivers based on migration of the quantities of subjects between the factors with opposing utilization trends;

rank the identified performance drivers based on the impact of the determined changes and the impact of the identified factors to produce results for the query;

receive updated data and feedback from a user over time;

adjust the threshold based on the updated data and continually detect changes in the sets of performance indicators over time for the performance drivers to alter the identified performance drivers based on the adjusted threshold and modify the ranking of the identified performance drivers;

store the feedback in a second database mapping the performance drivers of the modified ranking to corresponding characteristics;

train a supervised machine learning model over time with mappings from the second database to learn relationships between the characteristics of the performance drivers of the modified ranking and corresponding actions as the updated data and feedback from the user are received over time;

determine, via the supervised machine learning model, relationships between the performance drivers of the modified ranking and the corresponding actions;

modify the impact of the determined changes and the impact of the identified factors of the identified performance drivers based on the relationships determined by the supervised machine learning model;

alter the modified ranking of the identified performance drivers based on the modified impact of the determined changes and the modified impact of the identified factors; and adjust performance of actions based on the corresponding actions of the ranked performance drivers in the altered ranking to optimize performance of the healthcare related system.

* * * * *